United States Patent [19]
Selsted et al.

[11] Patent Number: 5,821,224
[45] Date of Patent: *Oct. 13, 1998

[54] ANTIMICROBIAL PEPTIDES FROM BOVINE NEUTROPHILS

[75] Inventors: Michael E. Selsted, Irvine; James S. Cullor, Woodland, both of Calif.

[73] Assignee: Regents of the University of California, Alameda, Calif.

[*] Notice: The term of this patent shall not extend beyond the expiration date of Pat. No. 5,459,235.

[21] Appl. No.: 356,832

[22] Filed: Dec. 13, 1994

Related U.S. Application Data

[63] Continuation of Ser. No. 33,873, Mar. 19, 1993, Pat. No. 5,459,235.

[51] Int. Cl.[6] .......................... A61K 38/17; C07K 14/47; C07K 16/18; C12N 15/12
[52] U.S. Cl. ........................... 514/12; 530/324; 530/300; 530/387.9; 530/388.1; 530/389.1; 514/2; 435/69.1; 536/23.5
[58] Field of Search .................................. 530/324, 300, 530/387.9, 388.1, 388.85, 389.1; 435/69.1; 514/2, 12; 536/23.5

[56] References Cited

U.S. PATENT DOCUMENTS

| | | | |
|---|---|---|---|
| 5,202,420 | 4/1993 | Zasloff et al. | 530/324 |
| 5,459,235 | 10/1995 | Selsted et al. | 530/300 |
| 5,550,109 | 8/1996 | Schonwetter et al. | 514/12 |
| 5,635,594 | 6/1997 | Lehrer et al. | 530/317 |

OTHER PUBLICATIONS

Lehrer et al., "Defensins: Endogenous Antibiotic Peptides of Animal Cells" *Cell* 64:229–230 (1991).
Selsted et al., "Determination of the Disulfide Array in the Human Defensin HNP–2" *J. Biol. Chem.* 264(7):4003–4007 (1989).
Bidlingmeyer et al., "Rapid Analysis of Amino Acids Using Pre–Column Derivatization" *J. Chromatogr.* 336:93–104 (1984).
Klemm, P., "Manual Edman Degradation of Proteins and Peptides" *In: Methods in Molecular Biology.* Walker, J.M. ed. Human Press, Clifton, NJ 1:243–254 (1984).
Edelhoch, H., "Spectroscopic Determination of Tryptophan and Tyrosine in Proteins" *Biochemistry* 6(7):1948–1954 (1967).
Pardi et al., "Solution Structures of the Rabbit Neutrophil Defensin NP–5" *J. Mol. Biol.* 201:625–636 (1988).
Hill et al., "Crystal Structure of Defensin HNP–3, an Amphiphilic Dimer: Mechanisms of Membrane Permeabilization" *Science* 251:1481–1485 (1991).
Lehrer et al., "Antimicrobial Polypeptides of Human Neutrophils" *Blood* 76(11):2169–2181 (1990).
Spitznagel, J.K., "Antibiotic Proteins of Human Neutrophils" *J. Clin. Invest.* 86:1381–1386 (1990).

Gennaro et al., "Neutrophil and Eosinophil Granules as Stores of Defense Proteins" *In: Blood Cell Biochemistry*, J.F. Harris, ed. Plenum Press, New York 335–368 (1991).
Ganz et al., "Defensins" *Eur. J. Haematol* 44:1–8 (1990).
Ganz et al., "Natural Peptide Antibiotics of Human Neutrophils" *J. Clin. Invest.* 76:1427–1435 (1985).
Selsted et al., "Primary Structures of Six Antimicrobial Peptides of Rabbit Peritoneal Neutrophils" *J. Biol. Chem.* 260(8):4579–4584 (1985).
Eisenhauer et al., "Purification and Antimicrobial Properties of Three Defensins from Rat Neutrophils" *Infect. Immun.* 57(7):2021–2027 (1989).
Eisenhauer et al., "Polymorphic Expression of Defensins in Neutrophils from Outbred Rats" *Infect. Immun.* 58(12):3899–3902 (1990).
Selsted et al., "Purification, Primary Structure, and Antimicrobial Activities of a Guinea Pig Neutrophil Defensin" *Infect. Immun.* 55(9):2281–2286 (1987).
Yamashita et al., "Purification, Primary Structure, and Biological Activity of Guinea Pig Neutrophil Cationic Peptides" *Infect. Immun.* 57:2405–2409 (1989).
Gennaro et al., "Potency of Bactericidal Proteins Purified from the Large Granules of Bovine Neutrophils" *Infect. Immun.* 40:684–690 (1983).
Gennaro et al., "A Novel Type of Cytoplasmic Granule in Bovine Neutrophils" *J. Cell. Biol.* 96:1651–1661 (1983).
Baggiolini et al., "Identification of Three Types of Granules in Neutrophils of Ruminants" *Lab. Invest.* 52(2):151–158 (1985).
Romeo et al., "Structure and Bactericidal Activity of an Antibiotic Dodecapetide Purified from Bovine Neutrophils" *J. Biol. Chem.* 263(20):9573–9575 (1988).
Frank et al., "Amino Acid Sequence of Two Proline–rich Bactenecins" *J. Biol. Chem.* 265(31):18871–18874 (1990).
Gennaro et al., "Purification, Composition, and Activity of Two Bactenecins, Antibacterial Peptides of Bovine Neutrophils" *Infect. Immun.* 57(10):3142–3146 (1989).
Selsted et al., "Indolicidin: a Novel Bactericidial Tridecapeptide Amide from Neutrophils" *J. Biol. Chem.* 267(7):4292–4295 (1992).
Amrein et al., "Prevention of Degradation of Human Polymorphonuclear Leukocyte Proteins by Diisopropylfluorophosphate" *Blood* 56(3):442–447 (1980).

(List continued on next page.)

*Primary Examiner*—Robert A. Wax
*Assistant Examiner*—Gabriele E. Bugalsky
*Attorney, Agent, or Firm*—Campbell & Flores LLP

[57] ABSTRACT

The present invention provides a new family of cysteine-rich antimicrobial peptides isolated from bovine neutrophils herein named beta defensins. Thirteen structurally homologous peptides were purified to homogeneity from a granule-rich cytoplasmic fraction of purified blood neutrophils. These antimicrobial compounds are useful in human and veterinary medicine, and as agents in agricultural, food science, and industrial applications.

9 Claims, 30 Drawing Sheets

OTHER PUBLICATIONS

Borregard et al., "Subcellular Localization of the b–Cytochrome Component of the Human Neutrophil Microbicidal Oxidase: Translocation during Activation" *J. Cell. Biol.* 97:52–61 (1983).

Fling et al., "Peptide and Protein Molecular Weight Determination by Electrophoresis Using a High–Molarity Tris Buffer System Without Urea" *Anal. Biochem.* 155:83–88 (1986).

Selsted et al., "Eosin Y: A Reversible Stain for Detecting Electrophoretically Resolved Protein" *Anal. Biochem.* 155:270–274 (1986).

Selsted et al., "Purification and Antibacterial Activity of Antimicrobial Peptides of Rabbit Granulocytes" *Infect. Immun.* 45(1):150–154 (1984).

Henschen, A.H., "5.1 Analysis of Cyst(e)ine Residues, Disulfide Bridges, and Sulfhydryl Groups in Proteins" *In: Advanced Methods in Protein Microsequence Analysis,* B. Wittmann–Liebold, J. Salnikow, and V.A. Erdman, eds. Springer–Verlag, Berlin 244–255 (1986).

Ambler, R.P., "Enzymatic Hydrolysis with Carboxypeptidases" *Methods Enzymol* 25:143–154 (1972).

Lehrer et al., "Ultrasensitive assays for endogenous antimicrobial polypeptides" *J. Immunol. Methods* 137:167–173 (1991).

Altschul et al., "Basic Local Alignment Search Tool" *J. Mol. Biol.* 215:403–410 (1990).

Fischer et al., "Identification of a mammalian glutaminyl cyclase converting glutaminyl into pyroglutamyl peptides" *Proc. Natl. Acad. Sci. USA* 84:3628–3632 (1987).

Zhang et al., "NMR Studies of Defensin Antimicrobial Peptides. 1. Resonance Assignment and Secondary Structure Determination of Rabbit NP–2 and Human HNP–1" *Biochem.* 31(46):11348–11356 (1992).

Pardi et al., "NMR Studies of Defensin Antimicrobial Peptides. 2. Three–Dimensional Structures of Rabbit NP–2 and Human HNP–1" *Biochem.* 31(46):11357–11364 (1992).

Chang et al., "High–level secretion of human growth hormone by *Escherichia coli*" *Gene* 55:189–196 (1987).

Neumann et al., "Gene Transfer into Mouse Lyoma Cells By Electroporation in High Electric Fields" *EMBO J.* 1(7):841–845 (1982).

Wade et al., "All–D amino acid–containing channel–forming antibiotic peptides" *Proc. Natl. Acad. Sci. USA* 87:4761–4765 (1990).

Sevier et al., "Monoclonal Antibodies in Clinical Immunology" *Clin. Chem.* 27(11):1797–1806 (1981).

Diamond et al. (1991) Proc. Nat. Acad. Sci., USA 88: 3952–3956.

Ganz et al. (1994) Curr. Opinions Immunol. 6: 584–589.

Martin et al. (1995) J. Leucocyte Biol. 58: 128–136.

FIG. 5

| | 1 | | | | | 10 | | | | | | | 20 | | | | | | | 30 | | | | | | | 40 | | |
|---|---|---|---|---|---|---|---|---|---|---|---|---|---|---|---|---|---|---|---|---|---|---|---|---|---|---|---|---|---|
| BNBD-1 | | | | | D | F | A | S | C | H | T | N | G | G | I | C | L | P | N | R | C | P | G | H | M | I | Q | I | G | I | C | F | R | P | R | V | K | C | C | R | S | W |
| BNBD-2 | P | E | G | V | R | N | H | V | T | C | R | I | N | R | G | F | C | V | P | I | R | C | P | G | R | T | R | Q | I | G | T | C | F | G | P | R | I | K | C | C | R | S | W |
| BNBD-3 | P | E | R | V | R | N | H | V | T | C | R | I | N | R | G | F | C | V | P | I | R | C | P | G | R | T | R | Q | I | G | T | C | F | G | P | R | I | K | C | C | R | S | W |
| BNBD-4 | P | E | V | V | R | N | P | Q | S | C | R | W | N | M | G | V | C | I | P | F | L | C | R | V | G | M | R | Q | I | G | T | C | F | G | P | R | V | P | C | C | R | R |   |
| BNBD-5 | P | E | G | V | R | N | P | Q | S | C | R | W | N | M | G | V | C | I | P | F | I | S | C | P | G | N | M | R | Q | I | G | T | C | F | G | P | R | V | P | C | C | R | R |
| BNBD-6 | P | E | G | V | R | N | H | V | T | C | R | I | N | R | G | F | C | V | P | I | R | C | P | G | R | T | R | Q | I | G | T | C | F | G | P | R | V | K | C | C | R | R | W |
| BNBD-7 | P | E | G | V | R | N | F | V | T | C | R | I | N | R | G | F | C | V | P | I | R | C | P | G | H | R | R | Q | I | G | T | C | L | G | P | Q | I | K | C | C | R | W |   |
| BNBD-8 | P | E | G | V | R | N | F | V | T | C | R | I | N | R | G | F | C | V | P | I | R | C | P | G | H | R | R | Q | I | G | T | C | L | G | P | Q | I | K | C | C | R | W |   |
| BNBD-9 | P | E | V | V | R | S | Y | L | S | C | W | G | N | R | G | I | C | L | L | N | R | C | P | G | R | M | R | Q | I | G | T | C | L | A | P | R | V | K | C | C | R |   |   |
| BNBD-10 | P | E | G | V | R | N | | | | G | P | L | S | C | R | R | N | G | G | V | C | I | P | I | R | C | P | G | R | M | R | Q | I | G | T | C | F | G | P | R | V | K | C | C | R | S | W |
| BNBD-11 | | | | | | | G | P | L | S | C | G | R | N | G | G | V | C | I | P | I | R | C | P | V | P | M | R | Q | I | G | T | C | F | G | P | R | V | K | C | C | R | S | W |
| BNBD-12 | | | | | | | G | P | L | S | C | G | R | N | G | G | V | C | I | P | I | R | C | P | V | P | M | R | Q | I | G | T | C | F | G | P | R | V | K | C | C | R | S | W |
| BNBD-13 | S | G | I | S | G | P | L | S | C | G | R | N | G | G | V | C | I | P | I | R | C | P | V | P | M | R | Q | I | G | T | C | F | G | P | R | V | K | C | C | R | S | W |

FIG. 6

```
                    T                              P
BNBD CONSENSUS:   S/S—C x x N x G h C h P I R C P G x x R Q I G T C h G R x h K C C R
TAP              N P V S—C V R N K G I C V P I R C P G S M K Q I G T C V G R A V K C C R K K
```

ANTIMICROBIAL PEPTIDES FROM BOVINE NEUTROPHILS

This application is a continuation of application Ser. No. 08/033,873, filed Mar. 19, 1993 U.S. Pat. No. 5,459,236.

This invention was made with Government support under Grant No. AI-22931, awarded by the National Institute of Health. The Government has certain rights in the invention.

Throughout this application, various publications are referred to within parenthesis to more fully disclose the state of the art. The disclosures of these references are hereby incorporated by reference.

BACKGROUND OF THE INVENTION

This invention relates generally to antimicrobial peptides, and, more specifically, to β-defensin peptides and their uses.

The cytoplasmic granules of polymorphonuclear leukocytes (neutrophils, PMN) contain numerous antimicrobial polypeptides which equip these cells to inactivate ingested microbial targets. These granule proteins constitute an antimicrobial arsenal which includes defensins, a family of broad spectrum antibiotic peptides which are released into the phagosome during phagolysosome fusion.

It has been previously demonstrated that the large granules of bovine neutrophils contain potent microbicidal peptides which are structurally distinct from defensins. These include three arginine-rich peptides, termed bactenecins, which efficiently kill several gram positive and gram negative bacteria in vitro. Recently, the isolation and characterization of a novel tridecapeptide amide from bovine neutrophils was reported. Termed indolicidin, this cationic peptide was shown to be unusually rich in tryptophan, and to have potent bactericidal activity against *E. coli* and *S. aureus*.

The ability to develop new therapeutics, especially against fungal and viral pathogens, is self evident. Discovery of new drugs of both classes is an urgent priority, as existing drugs are quite toxic and few in number.

In investigating the presence and biologic role of defensins in bovine neutrophils, a new antimicrobial peptide was discovered. Though possessing some features of defensins, namely their similar size, cationicity, and the presence of three intramolecular disulfides, the bovine peptides differ significantly in structure from defensins, and thus represent a new class of host defense peptides. To distinguish them from classical defensins, this novel peptide family is termed beta-defensins.

SUMMARY OF THE INVENTION

The present invention provides polypeptides useful as antimicrobial agents. Thirteen peptides from the granule-rich subcellular fraction of bovine neutrophils have been purified and characterized. These molecules possess broad spectrum antimicrobial activity at concentrations as low as 0.5 ug/ml. Common features of the peptides include their cationicity, and the presence of multiple cysteine residues. These peptides are useful as antimicrobial compounds in human or veterinary medicine, or as agents in agricultural, food science, or industrial applications.

BRIEF DESCRIPTION OF THE DRAWINGS

FIG. 5. Amino acid sequences of bovine neutrophil beta-defensins. The primary structures of BNBD 1–13 is shown in single letter code (SEQ ID NOS: 1–13). The sequences are aligned to demonstrate the most conserved amino acids which have been outline. The numbering of residues is indexed to the longest of the beta-defensin peptides.

FIG. 6. Amino acid sequence of bovine tracheal antimicrobial peptide (TAP) (SEQ ID NO: 15) and the beta-defensin consensus. The beta-defensin consensus consists of 27 residue positions in which the amino acid is absolutely conserved (11 residues) or where conservative or limited substitutions occur (16 residues):h, hydrophobic (=Leu, Ile, Val, or Phe); S/T, Ser or Thr; P/R, Pro or Arg. The disulfide connectivities as determined in BNBD-12 (ref. 31) are also shown.

FIG. 12A. Alignment indexed to the carboxyl terminal Cys-Cys dipeptides.

DETAILED DESCRIPTION OF THE INVENTION

Figure 1:
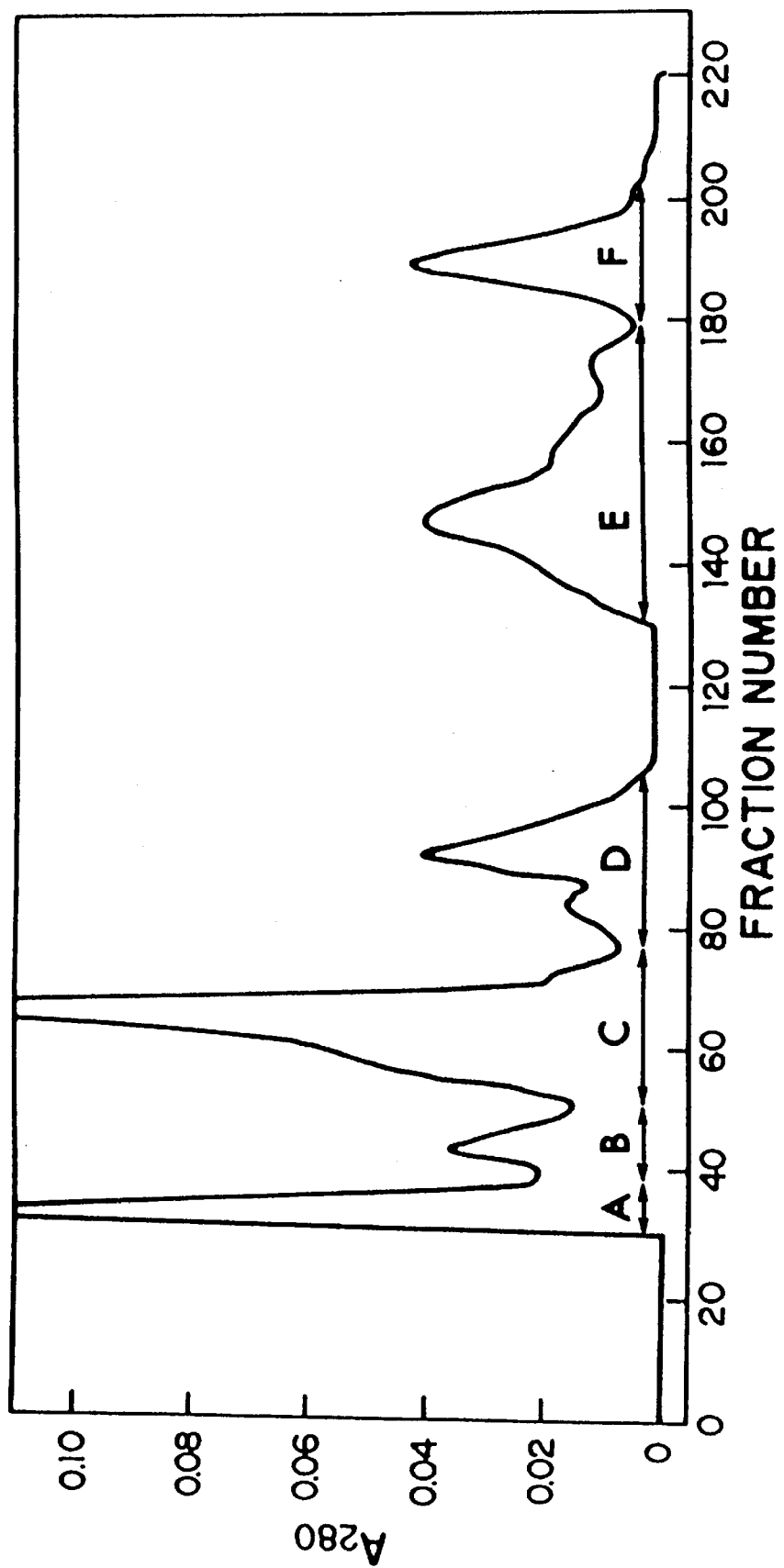
FIG. 1. Gel filtration chromatography of bovine neutrophil granule extract. Acetic acid extract of a granule-enriched fraction from $1.3 \times 10^{10}$ neutrophils was chromatographed on a Bio-Gel P-60 column as described in Materials and Methods. Fractions corresponding to Peak E were lyophilized and subjected to further purification as shown in FIG. 2.

The invention provides small peptide molecules, termed β-defensins, which express a broad range of antimicrobial activity, and for this reason are useful antimicrobial agents.

As used herein, the term "β-defensin" refers to peptides having generally between about 38 and 42 amino acids which make up a chain having a net charge of +4 to +10. Illustrative sequences are provided in FIG. 5. They are further characterized by their content of half-cysteine residues which are distributed in the peptide chain a a generally conserved fashion: the first and second half-cysteines are separated by 6 intervening residues; the second and third half-cysteines are separated by 4 intervening residues; the third and fourth half-cysteines are separated by 9 intervening residues; the fourth and fifth half-cysteines are separated by 6 intervening residues, and the fifth and six half-cysteines are adjacent. Furthermore, the cysteine residues are paired via disulfide bonds in a characteristic manner: the first cysteine to the fifth cysteine; the second cysteine to the fourth cysteine, and the third cysteine to the sixth cysteine. Some β-defensins are characterized by a pyroglutamate residue at the amino terminus which makes these molecules resistant to most aminopeptidases. β-defensins are further characterized by their broad range of antimicrobial activity.

It should be appreciated that various modifications can be made to the β-defensins amino acid sequence without diminishing the antimicrobial activity of the peptide. It is intended that peptides exhibiting such modifications, including amino acid additions, deletions or substitutions are within the scope of the invention.

This invention provides an isolated nucleic acid molecule which encodes an amino acid sequence corresponding to a β-defensin peptide. Examples of such nucleic acids include, but are not limited to the nucleic acids encoding BNBD-1 to −13. The invention also encompasses nucleic acid molecules which differ from that of the nucleic acid molecule which encode these amino acid sequences, but which produce the same phenotypic effect. These altered, but phenotypically equivalent nucleic acid molecules are referred to as "equivalent nucleic acids". And this invention also encompasses nucleic acid molecules characterized by changes in non-coding regions that do not alter the phenotype of the polypeptide produced therefrom when compared to the nucleic acid molecule described hereinabove. This invention further encompasses nucleic acid molecules which hybridize to the nucleic acid molecule of the subject invention. As used herein, the term "nucleic acid" encompasses RNA as well as single and double-stranded DNA and cDNA. In addition, as used herein, the term "polypeptide" encompasses any naturally occurring allelic variant thereof as well as man-made recombinant forms.

Use of the phrase "substantially pure" in the present specification and claims as a modifier of peptide or protein means that the peptide or protein so designated has been separated from its in vivo cellular environment. As a result of the separation and purification, the substantially pure peptides and proteins are useful in ways that the non-separated impure peptides or proteins are not.

As used herein, the term "substantially the same sequence" refers to a peptide sequence either identical to, or having considerable homology with, for example, the sequences BNBD-1 through BNBD-13 as shown in FIG. 5. It is understood that limited modifications can be made to the peptide which result in enhanced function. Likewise, it is also understood that limited modifications can be made without destroying the biological function of the peptide and that only a portion of the entire primary structure may be required in order to affect activity. For example, minor modifications of these sequences which do not completely destroy the activity also fall within this definition and within the definition of the compound claimed as such. Modifications can include, for example, additions deletions or substitutions of amino acid residues, substitutions with compounds that mimic amino acid structure or function as well as the addition of chemical moieties such as amino and acetyl groups. The modifications can be deliberate or can be accidental such as through mutation in hosts which produce β-defensin peptides exhibiting antimicrobial activity. All of these modifications are included as long as the peptide retains its antimicrobial activity.

As used herein, the term "antimicrobial activity" refers to the ability of a compound to inhibit or irreversibly prevent the growth of a microorganism. Such inhibition or prevention can be through a microbicidal action or microbistatic inhibition. Therefore, the term "microbicidal inhibition" as used herein refers to the ability of the antimicrobial compound to kill, or irrevocably damage the target organism. The term "microbistatic inhibition" as used herein refers to the growth of the target organism without death. Microbicidal or microbistatic inhibition can be applied to either an environment either presently exhibiting microbial growth (i.e., therapeutic treatment) or an environment at risk of supporting such growth (i.e., prevention or prophylaxis ).

As used herein, the term "environment capable of sustaining microbial growth" refers to a fluid, substance or organism where microbial growth can occur or where microbes can exist. Such environments can be, for example, animal tissue or bodily fluids, water and other liquids, food, food products or food extracts, crops and certain inanimate objects. It is not necessary that the environment promote the growth of the microbe, only that it permit its subsistence.

The following abbreviations are used herein: DFP, diisopropyl fluorophosphate; RP-HPLC, reversed phase high performance liquid chromatography; TGA, trifluoroacetic acid; HFBA, heptafluorobutyric acid; SDS; sodium dodecyl sulfate; DTT, dithiothreitol; PTH, phenylthiohydantoin; TSB, trypticase soy broth; PAGE, polyacrylamide gel electrophoresis; BNBD, bovine neutrophil beta-defensin; TFA, trifluoroacetic acid; TPCK, tosylamide-2-phenylethyl chloromethyl ketone; PITC, phenylisothiocyanate.

The β-defensin peptides of the present invention can be synthesized by methods well known in the art, such as through the use of automatic peptide synthesizers, by recombinant methods or well-known manual methods of peptide synthesis. In addition, they can be purified from natural sources such as white blood cells and possibly from various epithelia of vertebrate, preferably mammalian, origin. Such cells or tissues can be obtained from goats, sheep, bison and other such ruminants by means well known to those skilled in the art.

As used herein, β-defensin peptides encompass both naturally occurring and recombinant forms, i.e., non-naturally occurring forms of the protein and the polypeptide which are sufficiently identical to naturally occurring, β-defensin peptide to allow possession of similar biological activity. Examples of such polypeptides includes the polypeptides designated BNBD-1 to BNBD-13, but are not limited to them. Such protein and polypeptides include derivatives and analogs.

Also provided by this invention are the nucleic acid sequences encoding the β-defensin peptides, vectors and host cells containing them and methods of expression.

After the peptide of this invention is isolated, nucleic acids encoding the peptides are isolated by methods well known in the art, infra. These isolated nucleic acids can be ligated into vectors and introduced into suitable host cells for expression. Methods of ligation and expression of nucleic acids within cells are well known in the art, see Maniatis et al. (1989) (*Molecular Clonin: A Laboratory Manual.* Cold Spring Harbor Laboratory, Cold Spring Harbor, N.Y.), incorporated herein by reference.

Several types of vectors are available and can be used to practice this invention, e.g., plasmid, DNA and RNA viral vectors, baculoviral vectors, and vectors for use in yeast. When the vector is a plasmid, it generally contains a variety of components including promoters, signal sequences, phenotypic selection genes, origin of replication sites, and other necessary components as are known to those of skill in the art.

Promoters most commonly used in prokaryotic vectors include the lac Z promoter system, the alkaline phosphatase pho A promoter, the bacteriophage λPL promoter (a temperature sensitive promoter), the tac promoter (a hybrid trp-lac promoter that is regulated by the lac repressor), the tryptophan promoter, and the bacteriophage T7 promoter.

One other useful component of vectors used to practice this invention is a signal sequence. This sequence is typically located immediately 5' to the nucleic acid encoding the peptide, and will thus be transcribed at the amino terminus of the fusion protein. However, in certain cases, the signal sequence has been demonstrated to be located at positions other than 5' to the gene encoding the protein to be secreted. This sequence targets the protein to which it is attached across the inner membrane of the bacterial cell. The DNA encoding the signal sequence can be obtained as a restriction endonuclease fragment from any nucleic acid encoding a peptide that has a signal sequence. Suitable prokaryotic signal sequences can be obtained from genes encoding, for example, LamB or OmpF (Wong et al., *Gene* 68:193 (1983)), MalE, PhoA, OmpA and other genes. A preferred prokaryotic signal sequence for practicing this invention is the *E. coli* heat-stable enterotoxin II (STII) signal sequence as described by Chang et al., *Gene* 55:189 (1987).

Another useful component of the vectors used to practice this invention is a phenotypic selection gene. Typical phenotypic selection genes are those encoding proteins that confer antibiotic resistance upon the host cell. By way of illustration, the ampicillin resistance gene (amp), and the tetracycline resistance gene (tet) are readily employed for this purpose.

Construction of suitable vectors comprising the aforementioned components as well as the gene encoding the desired polypeptide are prepared using standard recombinant DNA procedures. Isolated DNA fragments to be combined to form the vector are cleaved, tailored, and ligated together in a specific order and orientation to generate the desired vector.

The DNA is cleaved using the appropriate restriction enzyme or enzymes in a suitable buffer. In general, about 0.2–1 μg of plasmid or DNA fragments is used with about 1–2 units of the appropriate restriction enzyme in about 20 μl of buffer solution. Appropriate buffers, DNA concentrations, and incubation times and temperatures are specified by the manufacturers of the restriction enzymes. Generally, incubation times of about one or two hours at 37° C. are adequate, although several enzymes require higher temperatures. After incubation, the enzymes and other contaminants are removed by extraction of the digestion solution with a mixture of phenol and chloroform and the DNA is recovered from the aqueous fraction by precipitation with ethanol.

To ligate the DNA fragments together to form a functional vector, the ends of the DNA fragments must be compatible with each other. In some cases, the ends will be directly compatible after endonuclease digestion. However, it may be necessary to first convert the sticky ends commonly produced by endonuclease digestion to blunt ends to make them compatible for ligation. To blunt the ends, the DNA is treated in a suitable buffer for at least 15 minutes at 15° C. with 10 units of the Klenow fragment of DNA polymerase I (Klenow) in the presence of the four deoxynucleotide triphosphates. The DNA is then purified by phenol-chloroform extraction and ethanol precipitation.

The cleaved DNA fragments are size-separated and selected using DNA gel electrophoresis. The DNA is electrophoresed through either an agarose or a polyacrylamide matrix. The selection of the matrix will depend on the size of the DNA fragments to be separated. After electrophoresis, the DNA is extracted from the matrix by electroelution, or, if low-melting agarose is used as the matrix, by melting the agarose and extracting the DNA from it.

The DNA fragments that are to be ligated together (previously digested with the appropriate restriction enzymes such that the ends of each fragment to be ligated are compatible) are put in solution in about equimolar amounts. The solution will also contain ATP, ligase buffer and a ligase such as T4 DNA ligase at about 10 units per 0.5 μg of DNA. If the DNA fragment is to be ligated into a vector, the vector is at first linearized by cutting with the appropriate restriction endonuclease(s). The linearized vector can then be treated with alkaline phosphatase or calf intestinal phosphatase. The phosphatasing prevents self-ligation of the vector during the ligation step.

After ligation, the vector with the foreign gene now inserted is transformed into a suitable host cell. Suitable prokaryotic host cells include *E. coli* strain JM101, *E. coli* K12 strain 294 (ATCC number 31,446), *E. coli* strain W3110 (ATCC number 27,325), *E. coli* X1776 (ATCC number 31,537), *E. coli* XL-1Blue (Stratagene), and *E. coli* B; however, many other strains of *E. coli*, such as HB101, NM522, NM538, NM539 and many other species and genera of prokaryotes can be used as well. In addition to the *E. coli* strains listed above, bacilli such as *Bacillus subtillis*, other enterobacteriaceae such as *Salmonella typhimunium* or *Serratia marcesans* and various *Pseudomonas* species can all be used as hosts.

Transformation of prokaryotic cells is readily accomplished using calcium chloride or other methods well known to those skilled in the art. Electroporation (Neumann et al., *ENBO J.* 1:841 (1982)) also can be used to transform these cells. The transformed cells are selected by growth on an antibiotic, commonly tetracycline (tet) or ampicillin (amp), to which they are rendered resistant due to the presence of tet and/or amp resistance genes on the vector.

After selection of the transformed cells, these cells are grown in culture and the plasmid DNA (or other vector with the foreign gene inserted) is then isolated. Plasmid DNA can be isolated using methods known in the art. This purified plasmid DNA is then analyzed by restriction mapping and/or DNA sequencing.

Following procedures outlined above, mammalian cell lines such as myeloma (P3-653), hybridoma (SP2/0), Chinese Hamster Ovary (CHO), Green monkey kidney (COS1) and murine fibroblasts (L492) are suitable host cells for polypeptide expression. These "mammalian" vectors can include a promoter, an enhancer, a polyadenylation signal, signal sequences and genes encoding selectable markers such as geneticin (neomycin resistance), mycophenolic acid (xanthine guanine phosphoribosyl transferase) or histidinol (histidinol dehydrogenase).

Suitable promoters for use in mammalian host cells include, but are not limited to, Ig Kappa, Ig Gamma, Cytomegalovirus (CMV) immediate early, Rous Sarcoma Virus (RSV), Simian virus 40 (SV40) early, mouse mammary tumor (MMTV) virus and metallothionein. Suitable enhancers include, but are not limited to Ig Kappa, Ig Heavy, CMV early and SV40. Suitable polyadenylation sequences include Ig Kappa, Ig Gamma or SV40 large T antigen. Suitable signal sequences include Ig Kappa, Ig Heavy and human growth hormone (HGH).

When the vector is baculovirus, suitable promoters and enhancer sequences include, but are not limited to AcMNPV polyhedrin, AcMNPV ETL and AcMNPV p10 sequences. One particularly suitable polyadenylation signal is the polyhedrin AcMNPV. Ig Kappa, Ig Heavy and AcMNPV are examples of suitable signal sequences. These vectors are useful in the following insect cell lines, among others: SF9, SF21 and High 5.

Alternatively, the polypeptides can be expressed in yeast strains such as PS23-6A, W301-18A, LL20, D234-3, INVSC1, INVSC2, YJJ337. Promoter and enhancer sequences such as gal 1 and pEFT-1 are useful. Vra-4 also provides a suitable enhancer sequence. Sequences useful as functional "origins of replication" include arsl and 2µ circular plasmid.

This invention further provides the peptides produced recombinantly. Methods of producing the peptides recombinantly alos is within the scope of this invention. This method comprises growing the host cell containing a nucleic acid encoding a peptide under suitable conditions such that the nucleic acid is transcribed and/or translated and isolating the peptide so produced.

Alternatively, the β-defensin antimicrobial peptides can be chemically synthesized using synthesis procedures known to one skilled in the art. Preferably, an automated peptide synthesizer such as Milligen, Model 9050 (Milligen, Milliford, Mass.) is used in conjunction with $N^\alpha$-Fmoc amino acids on a polyethylene glycol-polystyrene (PEG-PS) graft resin. Suitable linkers such as a peptide amide linker (PAL) can be used, for example, to create carboxamide end groups.

Numerous modifications are contemplated according to this invention. Besides the obvious approach of replacement of specific residues in the natural sequence, an alternative embodiment involves synthesis of the peptide from D-amino acids thus minimizing potential inactivation by proteases. Such means are well known in the art. See, for example, Wade et al., *PNAS, USA* 87:4761–4765 (1990).

Anti-β-defensin antibodies can be made by methods conventional in the art. For example, polyclonal antiserum can be raised in appropriate animals, such as rabbits, mice, or rats. β-defensin peptides, either synthetic or naturally obtained, can be used to immunize the animal. The immunogen can then be used to immunize animals by means well known to those skilled in the art. Serum samples are collected until the anti-β-defensin titer is appropriate. Various fractions of the antisera, such as IgG, can be isolated by means well known in the art. Alternatively, β-defensin immunogens can be used to obtain monoclonal antibodies, again by means well known in the art, see for example Harlow and Lane, *Antibodies: A Laboratory Manual*, (Cold Springs Harbor Laboratory, 1988).

The antimicrobial, or antibacterial, activity of β-defensins can be measured against various pathogens. Microorganisms are grown to appropriate concentration, mixed with an appropriate medium, such as an agarose-typticase soy medium, and contacted with solutions of the β-defensins. After appropriate incubation, the antimicrobial activity is apparent from clear zones surrounding the antibacterial samples. The clear zones are concentration dependent. Anti-β-defensin antibodies can be used to determine the presence of β-defensin in biological samples, such as histological samples. An appropriate detectable second antibody can then be used to identify such as by visualization, the primary antibody attached to the β-defensin. Means of detection include the use of radioactive nucleotides or enzyme substrates such as peroxidase.

β-defensins, either purified from natural sources or synthetic, can be administered to a subject in need of therapy by various means, including oral administration, preferably in a slow-release type formulation which will avoid release within the stomach. Alternatively they can be administered through nasalgastric intubation or transabdominal catheter. Individual species of β-defensins can be administered singly or a combination can be administered simultaneously or sequentially.

Defensins were the first antimicrobial peptides isolated from leukocytes, and until reported by the present inventors, were the only phagocyte-derived molecules known which contain a conserved tri-disulfide structural motif. Though classical defensins were not detected in bovine neutrophils, the search for them led to the discovery of a new class of distinct but related peptide antibiotics. The beta-defensins constitute a highly conserved family of at least 13 neutrophil peptides which are characterized by a disulfide motif different from that of the defensin family. Also disclosed herein is the determination of the disulfide structure in BNBD-12 and possible structural relationships between classical and beta-defensins which emerge from a comparison of the respective cysteine connectivitites.

Unlike classical defensins which have free amino termini, 7 of the 13 beta-defensins were found to be blocked at the N-terminus with a pyroglutamyl residue which results from the enzymatic cyclization of N-terminal glutamine. Three of the beta-defensins appear to be amino terminal processing variants of corresponding peptides which are slightly longer. The sequences of BNBD-2 and BNBD-8 are identical to BNBD-3 and BNBD-9 respectively, except that the latter two peptides each have any pyroglutamyl-glycine dipeptide extension. In addition, BNBD-12 and BNBD-13 have identical sequences except that BNBD-13 has a Ser-Gly-Ile-Ser amino terminal tetrapeptide (FIG. 5).

As measured in in vitro studies, BNBD-2 and -3 have equivalent antibacterial activity against both test organisms. Similarly, the antibacterial activities of BNBD-12 and BNBD-13 are approximately equal. In contrast, the BNBD-8 and -9 pair differ in antibacterial potency, with the more abundant BNBD-9 having the greater in vitro activity (FIG. 7). This difference in activity reveals that the N-terminus is a structural determinant of function, much as the N-terminus of human defensins plays a role in antimicrobial potency and function in the host defense of other tissues as well.

In a preferred embodiment, the present invention provides a therapeutic antimicrobial. Although antibacterial antibiotics are plentiful, antifungals are few in number. One or more of the peptides, may have utility as antifungal agents, either alone, or as lipid vesicle preparations. The latter approach has been used with success with the non-peptide antifungal drug amphotericin. Specific applications would be dependent on the pathogen targeted. For example, C. albicans, the common cause of mucocutaneous fungal disease in AIDS patients, which is extremely susceptible to several β-defensins, might be controlled in these individuals more effectively by a β-defensin-based therapeutic or in combination with existing first line drugs. Similarly, β-defensins may be used as a therapeutic in veterinary medicine.

In a further embodiment, the present invention may be used as a food preservative or in treating food products to eliminate potential pathogens. The latter use might be targeted to the shell fish and poultry industries which have serious problems with enteric pathogens which cause severe human disease.

In another embodiment, β-defensins may be used as disinfectants, for use in any product which must remain microbe-free.

In a further embodiment, β-defensins may be used as antimicrobials for food crops, either as agents to reduce post harvest spoilage, or expressed transgenically to enhance host resistance.

In certain embodiments of the invention, the treatment of the soluble proteins comprises size exclusion chromatography, ion-exchange chromatography, or reverse-phase, high performance, liquid chromatography. It will be appreciated by one skilled in the art, however, that treatment of soluble proteins to purify polypeptides may be accomplished by many methods known to those skilled in the art, all of which are contemplated by this invention. Further, in one embodiment of the invention, the treatment of granulocytes so as to recover granules comprises density gradient centrifugation.

The invention also provides a composition which comprises the purified polypeptide in an amount effective to kill bacteria or fungi and a suitable carrier. Such composition may be used in numerous ways to combat bacteria or fungi, for example, in household or laboratory antimicrobial formulations using carriers well known in the art.

The invention further provides a pharmaceutical composition for treating a human bacterial or fungal infection which comprises the purified polypeptide of the invention in an amount effective to treat a human bacterial or fungal infection and a pharmaceutically acceptable carrier.

It should be understood that the compositions of the present invention have activity against a wide variety of microorganisms, such as fungi, bacteria (both gram positive and negative), and protozoa and viruses. Different compositions will have differing degrees of activities towards different organisms. The peptides of the present invention may also be combined with other proteins to act as preservatives to protect the proteins against bacterial degradation. Alternatively, the subject polypeptides or compositions may be used as preservatives and disinfectants in a wide variety of formulations, such as contact lens solutions, ointments, shampoos, medicaments, foods, and the like. The amount of the polypeptide which is employed in the compositions may vary depending upon the nature of the other components, the degree of protection required and the intended use of the composition.

Where the polypeptides are to be used as antimicrobial agents, they can be formulated in buffered aqueous media containing a variety of salts and buffers. The salts will for the most part be alkali and alkaline earth halides, phosphates and sulfates, e.g., sodium chloride, potassium chloride or sodium sulfate. Various buffers may be used, such as citrate, phosphate, HEPES, Tris or the like to the extent that such buffers are physiologically acceptable to the host which is being treated.

Various excipients or other additives may be used, where the compounds are formulated as lyophilized powders, for subsequent use in solution. The excipients may include various polyols, inert powders or other extenders.

Depending on the nature of the formulation and the host, the subject compounds may be administered in a variety of ways. The formulations may be applied topically, by injection, e.g., intravenously, intra peritoneally, etc., nasopharyngeally, etc.

The invention further provides a method for killing bacteria or fungi which comprises contacting the bacteria or fungi with an effective amount of the compositions described above. Effective amounts may be readily determined by those skilled in the art.

The invention further provides a method for treating a subject having a bacterial or fungal infection which comprises administering to the subject an effective amount of the pharmaceutical composition described above.

In another aspect of the invention, the composition comprising the purified polypeptide of the invention in an amount effective to kill bacteria or fungi and a suitable carrier; and the pharmaceutical composition for treating a human bacterial or fungal infection which comprises the purified polypeptide of the invention in an amount effective to treat a human bacterial or fungal infection and a pharmaceutically acceptable carrier may additionally comprise a detergent. The addition of a detergent to such compositions is useful to enhance the antibacterial or antifungal characteristics of the novel polypeptide of the invention. Although any suitable detergent may be used, the presently preferred detergent is a nonionic detergent, such as Tween 20 or 1% NP40.

The invention also provides a pharmaceutical composition for treating a human bacterial or fungal infection which comprises the purified polypeptide of the invention in an amount effective to treat a human bacterial or fungal infection incorporated into a pharmaceutically acceptable liposome.

It will be readily understood by those skilled in the art that any suitable pharmaceutically acceptable liposome may be used as a vehicle for the polypeptide of the present invention. Such liposomal compositions have activity against a wide variety of microorganisms similar to the activity of other compositions of this invention discussed in more detail above. Additionally, these compositions may be administered in a variety of conventional and well-known ways as is also discussed in greater detail above.

The following examples are intended to illustrate but not limit the invention.

EXAMPLE I

Materials and Methods

Bovine neutrophils. Polymorphonuclear leukocytes (PMN) were purified from 1 L batches of fresh citrated bovine blood. Following sedimentation at 40 minutes at 700×g and 37° C., the erythrocyte column was subjected to 7 seconds of hypotonic lysis, after which isotonicity was restored using 3×phosphate buffered saline. The leukocyte-rich suspension was then sedimented at 120×g (4° C., 15 minutes). Residual erythrocytes were lysed by repeating this procedure 1 or 2 times. Aliquots were removed for quantitation by homocytometry and differential counts. Preparations obtained by this procedure contained an average of $4 \times 10^9$ cells per L of whole blood of which 97±3% were neutrophils. Half of the preparations were treated with 2 mM disopropylfluorophosphate (DFP;20). Neutrophil preparations were then cooled to 4° C. for 20 minutes and disrupted by nitrogen cavitation in a Parr bomb (21). The cavitate was centrifuged at 800×g for 10 minutes at 4° C., and the granule-containing supernatant was collected. Granules were harvested by centrifugation at 27,000×G for 40 minutes and stored at −80° C.

PMN Granule extracts. Preparations of frozen granules from $1-5 \times 10^{10}$ PMN were extracted with 5 ml of ice cold 10% acetic acid per $1 \times 10^9$ cell equivalents. After stirring on ice for 18 hours, the suspension was clarified by centrifugation at 27,000×G for 20 minutes at 4° C. and the supernatants were lyophilized and stored at −70° C.

Size exclusion chromatography. Lyophilized granule extract was dissolved in 10% acetic acid at a concentration of ca. $1 \times 10^9$ cell equivalents per ml, clarified by centrifugation, and loaded onto a 4.8×110 cm column of BioGel P-60 equilibrated in 5% acetic acid. The column was run at 8° C. with an elution rate of 2 cm per hour, and 15 ml fractions were collected with continuous monitoring at 280 nm.

Reversed phase HPLC (RP-HPLC). Low molecular weight components eluting from the size exclusion column were further resolved by RP-HPLC on a Waters 510 binary system on a 1×25 cm Vydac C-18 column. Water and acetonitrile containing 0.1% trifluoroacetic acid (TFA) or 0.13% heptafluorobutyric acid (HFBA) were used for gradient elution. Purified peptides were lyophilized, dissolved in 0.01% acetic acid at 500 pg/ml, and stored at −70° C.

Polyacrylamide gel electrophoresis. Sodium dodecyl sulfate (SDS; Fling et al., *Anal. Biochem.* 155:83–88 (1986)) and acid-urea (Selsted et al., Anal. Biochem. 155:270–274 (1986)) gel electrophoresis were used to the estimate molecular mass and/or purity of protein preparations (Selsted et al., *Infect. Immun.* 45:150–154 (1984)).

Amino acid analysis. The amino acid composition of each peptide was determined on 6N HCl hydrolysates (2 hours, 150° C.) of native and performic acid-oxidized, or reduced and alkylated samples (Bindlingmeyer et al., *J. Chromatogr.* 336:93–104 (1984)). Tryptophan content was determined by sequence analysis and by spectroscopic measurement on a Beckman DU 60 spectrophotometer (Endelhoch, *Biochem.* 6:1948–1954 (1967)).

Sequence Analysis. Samples for sequence analysis were reduced with DTT and alkylated with vinyl pyridine or iodocetamide (Henschen, *Advanced Methods in Protein Microseq. Anal.*—Springer-Verlag Berlin 244–255 (1986)), and purified by RP-HPLC. Two cycles of manual Edman degradation (Klemm, infra)) were performed on all samples to identify N-terminally blocked peptides. Three to 4 nmol of each N-blocked peptide was incubated with 2 µg of pyroglutamate amino peptidase (Boehringer Mannheim) for 5 hours at room temperature in 50 µl of 0.1M sodium phosphate, 0.01M disodium EDTA, 5 mM DTT, 5% glycerol, pH 8.0. The deblocked peptide was then purified by RP-HPLC prior to automated Edman sequence analysis. Automated sequence analysis was performed on an Applied Biosystems 475A instrument configured with on-line PTH-amino acid analysis.

Carboxyl terminal amino acids were determined by amino acid analysis of residues release by carboxypeptidases A or Y (Ambler, *Methods Enzymol.* 25:143–154 (1972)). Approximately 1 nmol of S-alkylated peptide was dissolved in 50 µl of 0.05M sodium phosphate buffer, pH 8.0 or 0.125M ammonium bicarbonate, pH 8.0, containing 3 to 6 µg of carboxypeptidase A (Boehringer Mannheim) for 20 to 60 minutes at 37° C. Released tryptophan was identified by its co-elution with authentic tryptophan on RP-HPLC.

Mass spectrometry. Native peptide mass was determined by positive ion fast atom bombardment mass spectrometry on a VG 7070E-HF instrument. Scans were from 3450–6200 m/z at a scan speed of 300 seconds per decade with a resolution of 500 for 5 cumulative scans. Ions were generated by bombardment of the meta-nitrolbenyl alcohol matrix by a neutral xenon atom beam accelerated under an 8 kv potential.

Trypsin and chymotrypsin treatment. Proteolytic digestion of selected peptides was carried out with α-chymotrypsin (Boehringer Mannheim) or tosylamide-2-phynylethyl chloromethyl ketone-treated trypsin (Worthington). S-pyridylethylated peptide (ca. 2 nmol) was dissolved in 50 µl 0.125M ammonium bicarbonate and incubated with 0.2 µg of enzyme at 37° C. for 1 to 5 minutes. Peptide fragments were purified by RP-HPLC, characterized by amino acid analysis, and in some cases sequenced.

Antimicrobial assay. Escherichia coli ML35 and Staphylococcus aureus 502A were utilized in a radial diffusion assay recently described by Lehrer et al. (*J. Immunol. Meth.* 167–173 (1991)). Bacteria were grown to mid-log phase in trypticase soy broth (TSB), diluted into 10 ml of warm (43° C.) 1% agarose containing 3 mg of TSB, buffered with 10 mM sodium phosphate, pH 7.4. Five µl of each peptide solution was pipetted into wells formed with a 4 mm cork bored and allowed to incubate at 37° C. for 3–4 hours. Plates were then overlaid with 10 ml of sterile 1% agar containing 2×TSB. Following incubation for 18 to 24 hours, the diameter of the clear zone surrounding each well was measured using a magnified transilluminator.

EXAMPLE II

Results

Purification of bovine neutrophil peptides. Previous electrophoretic analyses of the acid-soluble proteins of bovine PMN granules demonstrated that these preparations contain a complex mixture of proteins varying in size from 1000 to 200,000 D. In order to isolate putative defensins from bovine neutrophil granules, $1-3\times10^{10}$ cell equivalents of acid solubilized granule protein was fractionated on a Bio-Gel P-60 column and antibacterial activity in pooled eluent fractions was assayed as described in Methods. Each of the peaks (A-F in FIG. 1) contained bactericidal activity against *S. aureus* and *E. coli* (data not shown). As described in a recent report, Peak F was predominantly comprised of indolicidin, a novel thirteen residue antibiotic peptide amide (Selsted et al., *J. Biol. Chem.* 267:4292–4295 (1992)).

SDS-PAGE of pooled fractions from the P-60 column indicated that most of the proteins eluting in peak E were ca. 5 kD (data not shown), and amino acid analysis demonstrated that the overall cysteine content of material in this peak was ca. 15%. Since these are features consistent with the size and composition of defensins, peak E fractions were combined and further purified by HPLC.

Figure 2:
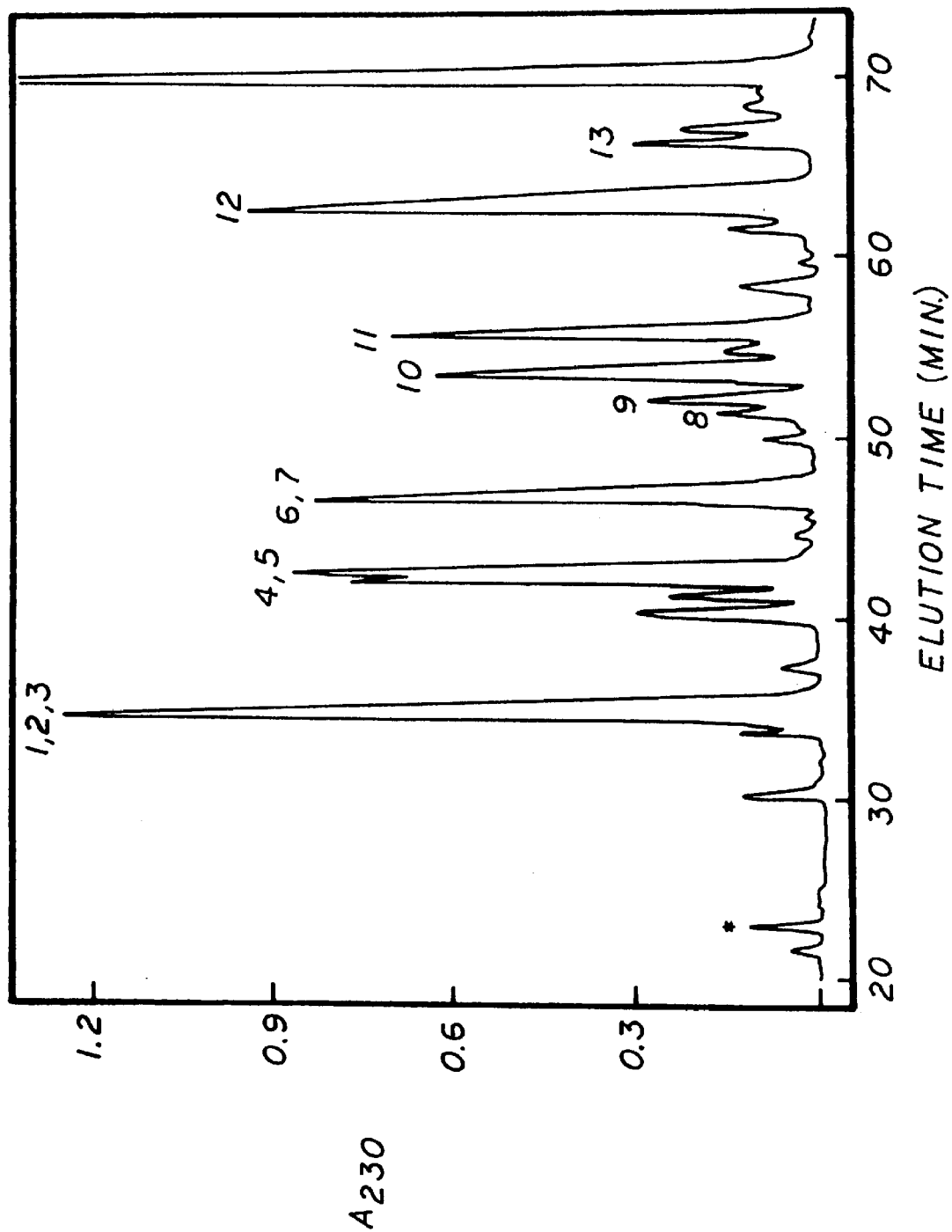
FIG. 2. Reversed phase HPLC of Peak E fractions. One tenth of the pooled fractions from Peak E (FIG. 1) was loaded on a 1×25 cm Vydac C-18 column equilibrated in 0.1% TFA/water (solvent A) at a flow rate of 3.0 ml/minute. A linear gradient of acetonitrile (20% to 45%) containing 0.1% TFA (solvent B) was applied at the rate of 0.33% per minute. Fractions were collected using the peak cutting mode of a Pharmacia Frac-200 fraction collector. The identity of the beta-defensin(s) eluting in each peak is indicted by the numbers 1 to 13 which corresponds to the nomenclature in Table I and FIG. 5.
Figure 3:
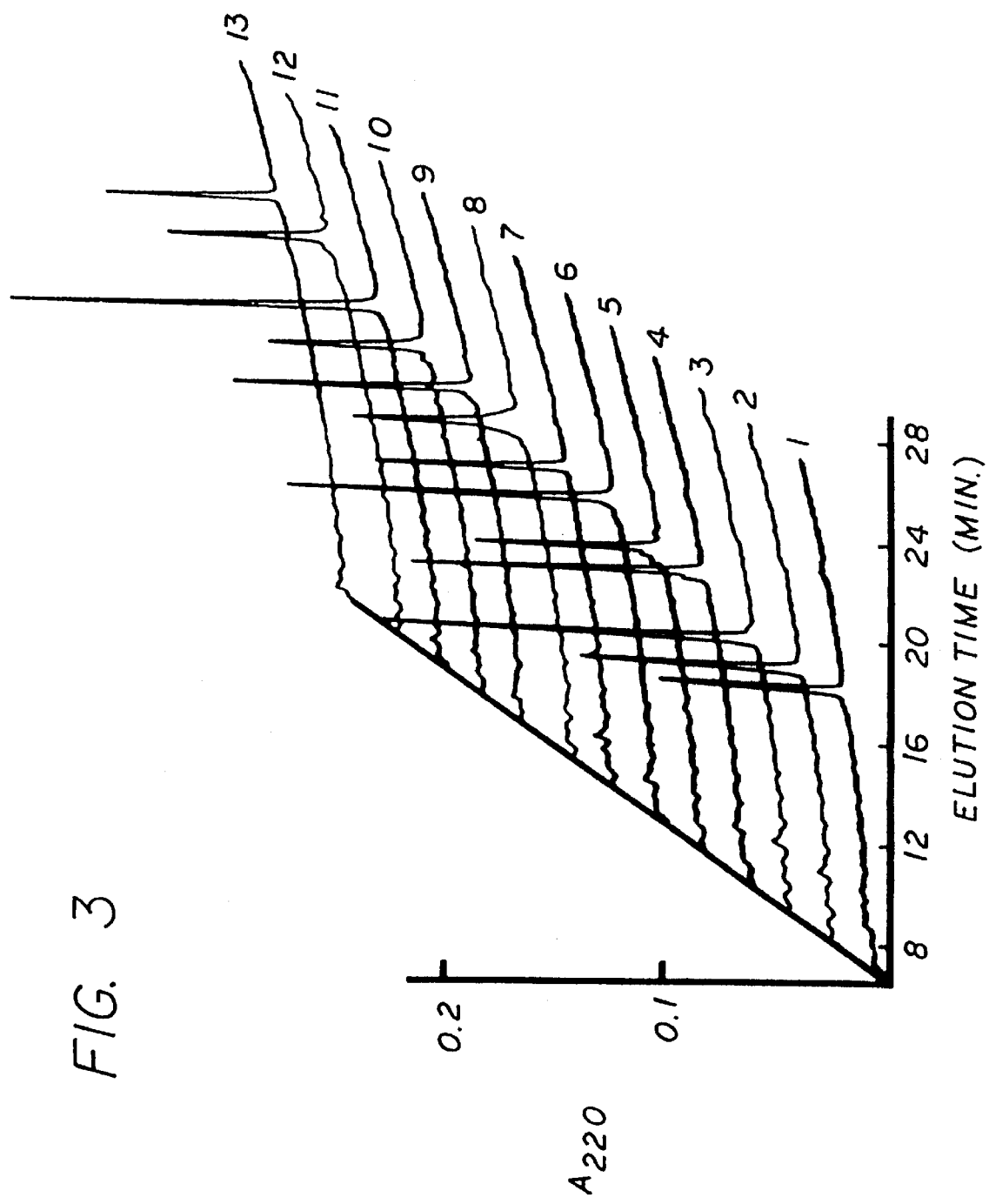
FIG. 3. Analytical RP-HPLC of purified beta-defensins 0.5 to 1 μg of each purified peptide was injected onto a 0.4×25 cm Vydac C-18 column run at a flow-rate of 1.0 ml/minute. Solvents are the same as in FIG. 2. Gradient conditions: 10% B to 50% B in 25 minutes.
Figure 4:
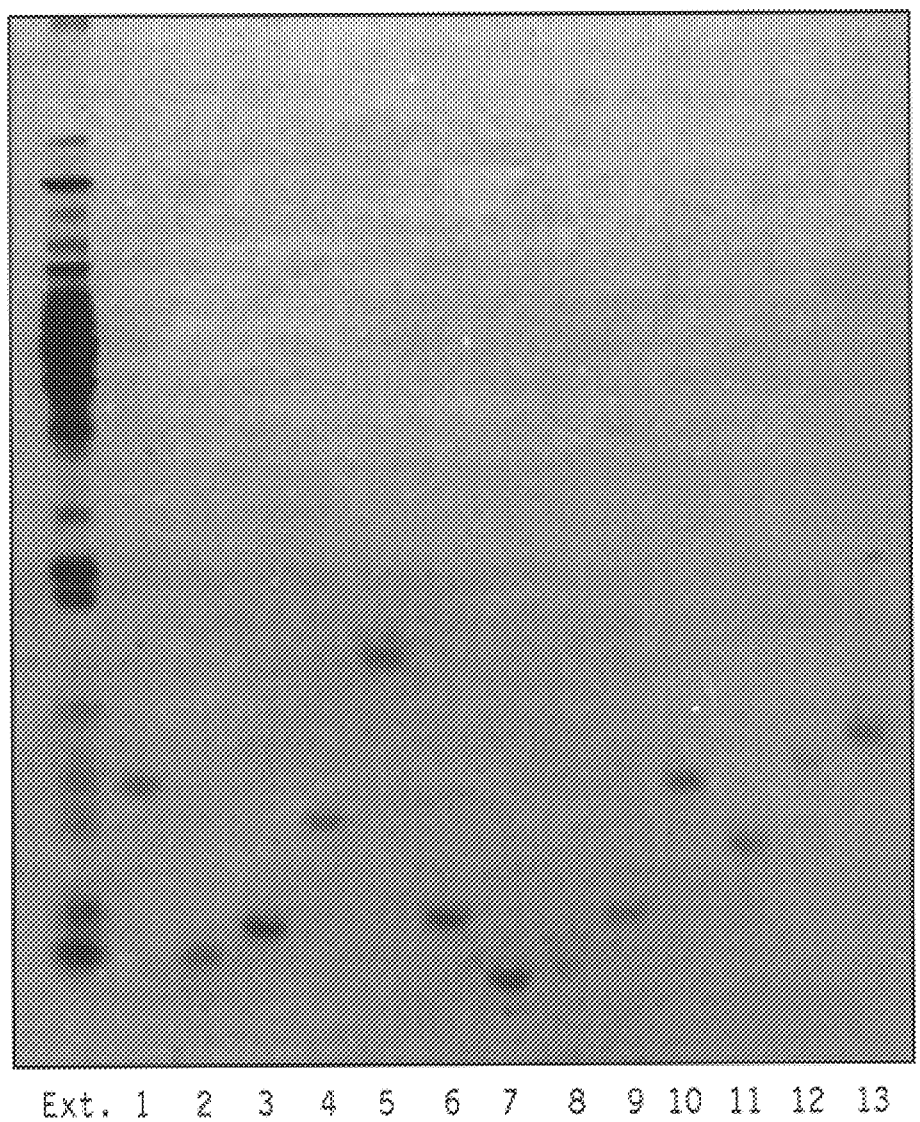
FIG. 4. Acid-urea gel of purified beta-defensins A 2 μg sample of each peptide was loaded onto a 12.5% acid-urea polyacrylamide gel which was electrophoresed for 4 hours at 250 V. A 100 μg sample of crude acid extract from bovine neutrophil granules (Ext.) was run in parallel. Staining was with Coomassie Blue containing 15% formalin.
Figure 7A:
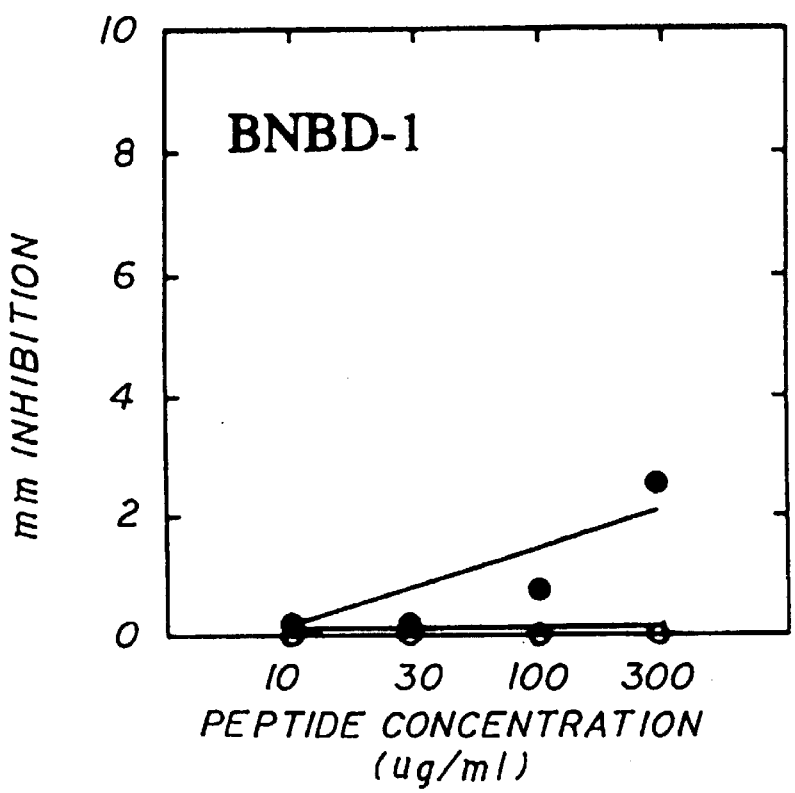
FIG. 7. Antibacterial activities of purified beta defensins. Nutrient agar plates seeded with *E. coli* ML35 (● or *S. aureus* 502A (○) were used to assess antibacterial activity of 13 neutrophil beta-defensins in addition to rabbit defensin NP-1, bactenecin dodecapeptide, and indolicidin. Activity is expressed as the diameter of clearing (mm) resulting from the application of 5 μl of peptide at the concentrations shown.
Figure 7B:
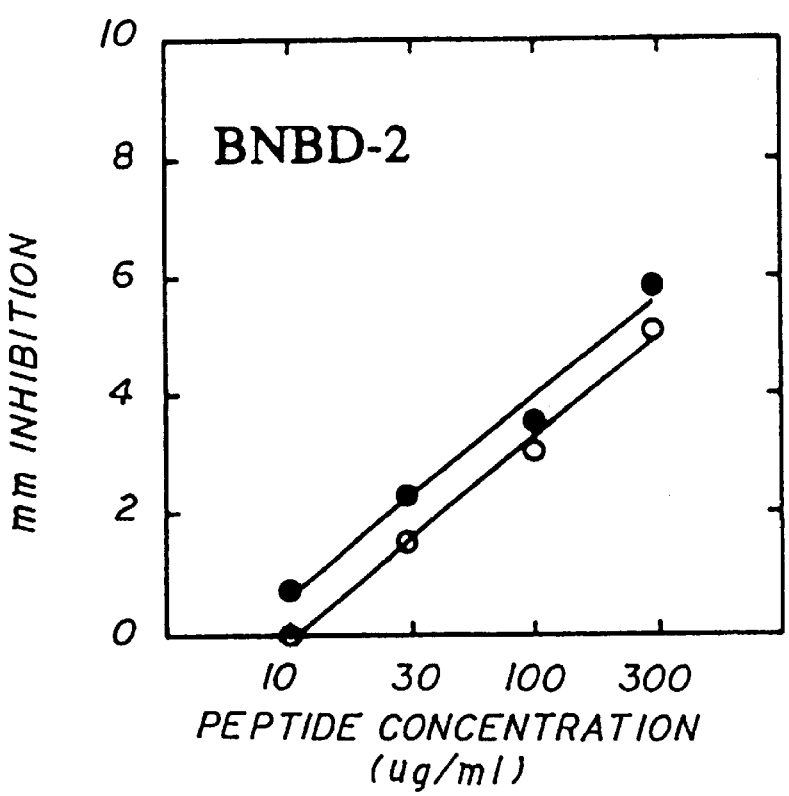
Figure 7C:
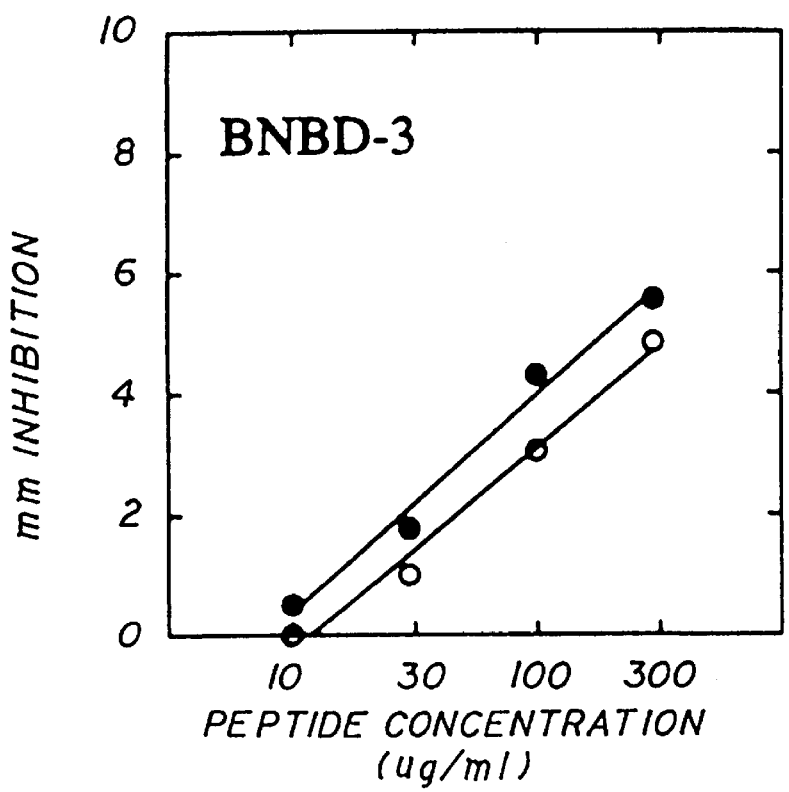
Figure 7D:
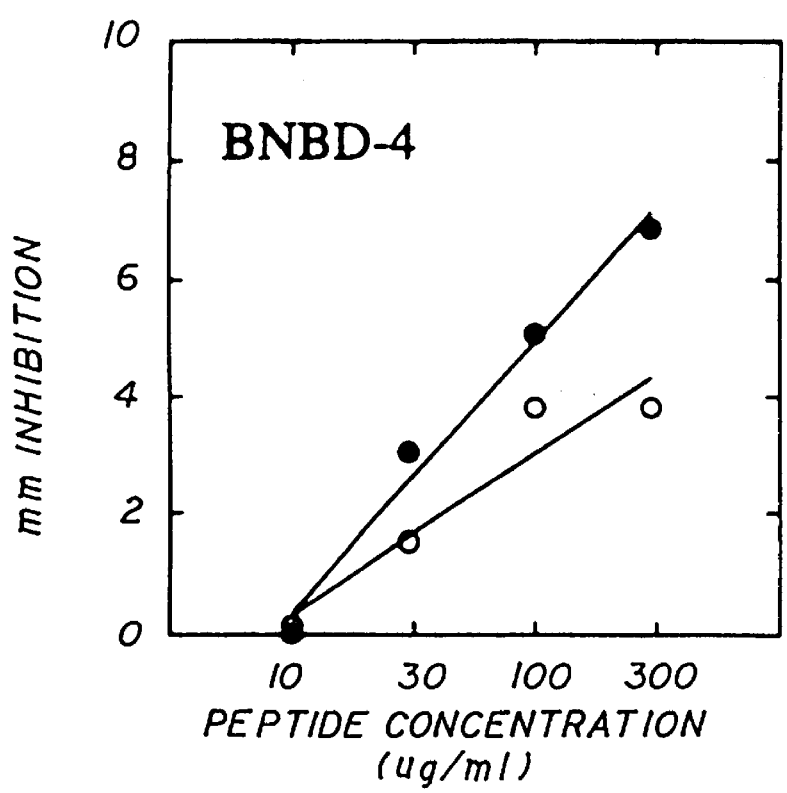
Figure 7E:
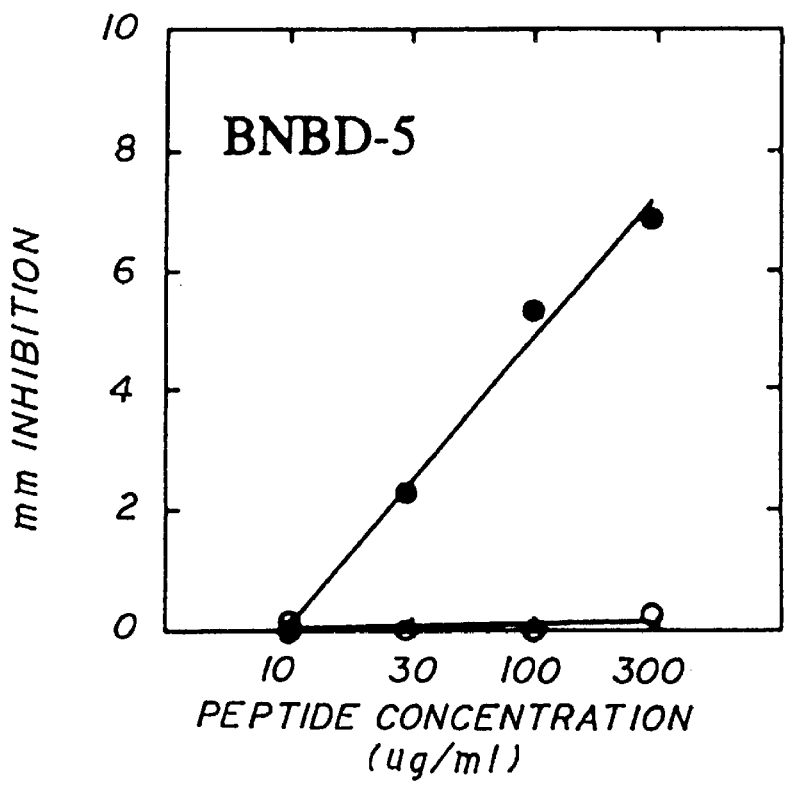
Figure 7F:
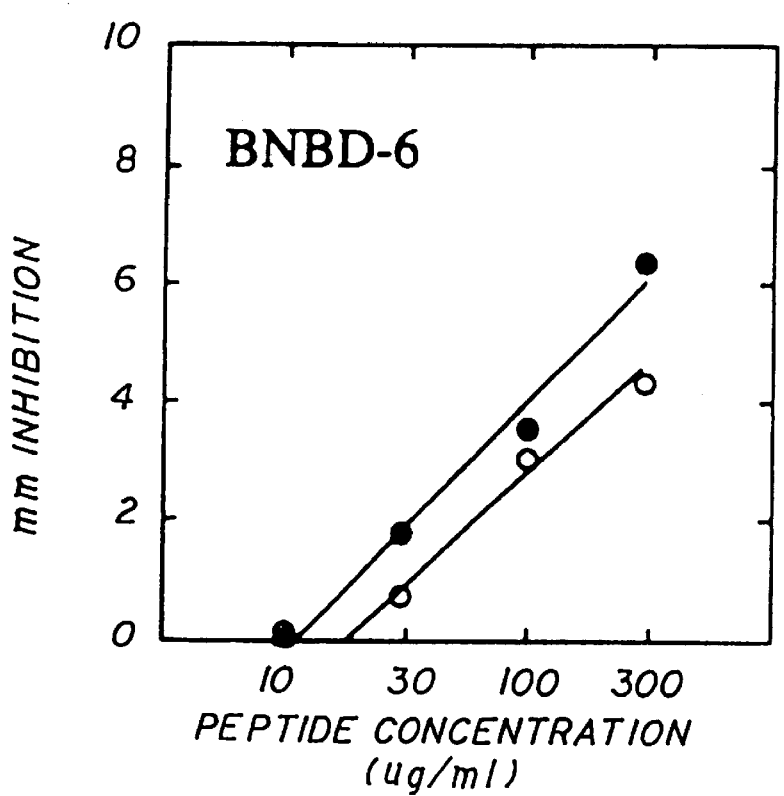
Figure 7G:
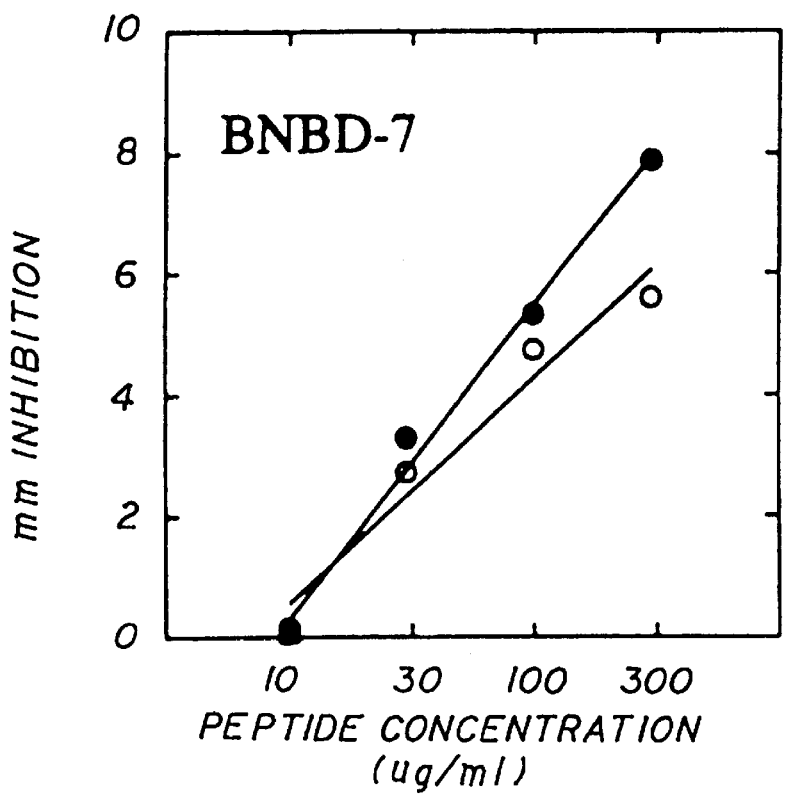
Figure 7H:
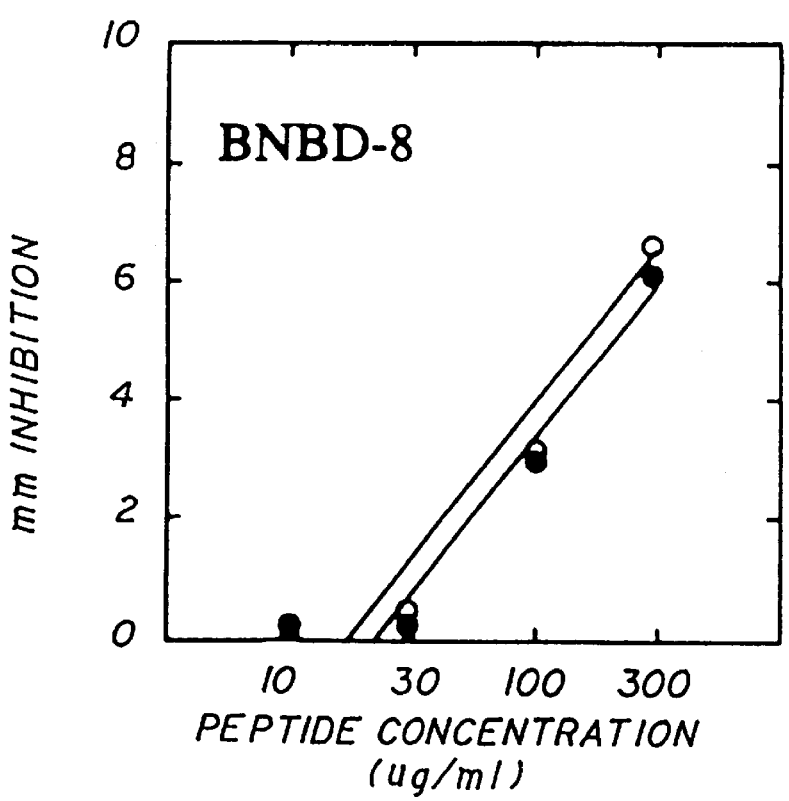
Figure 7I:
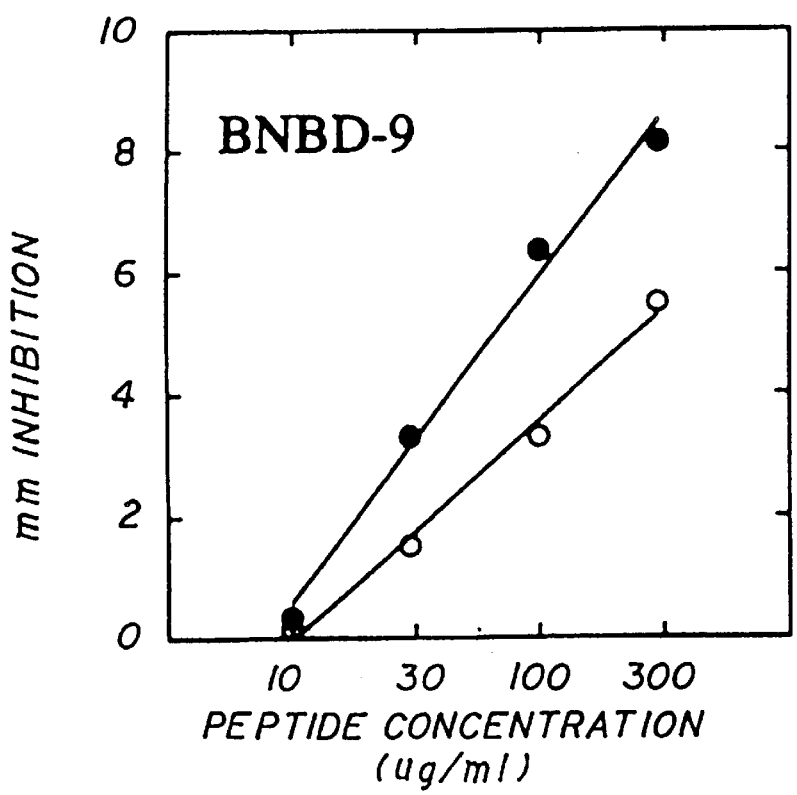
Figure 7J:
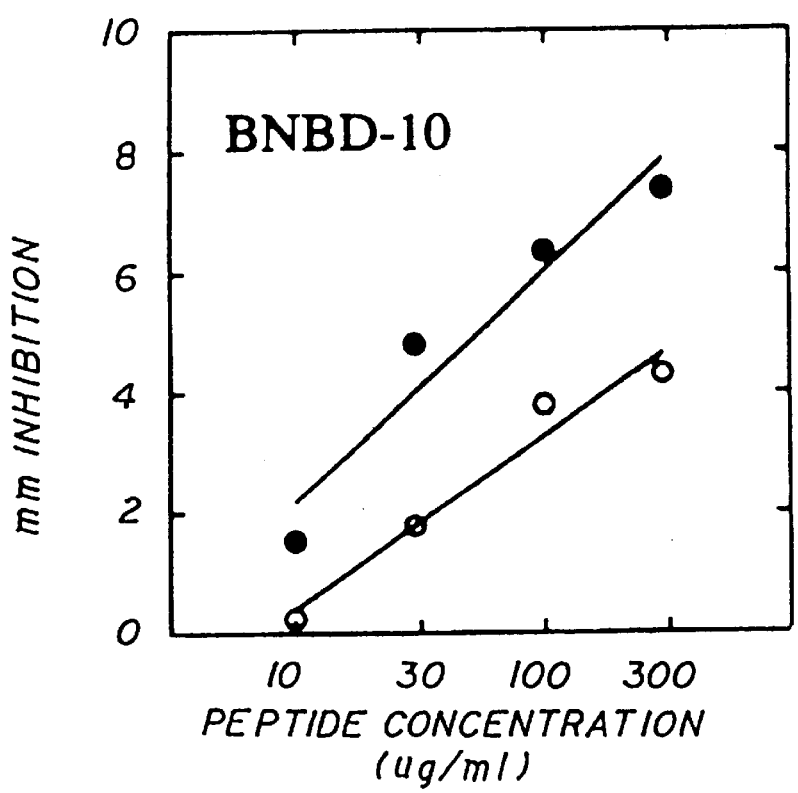
Figure 7K:
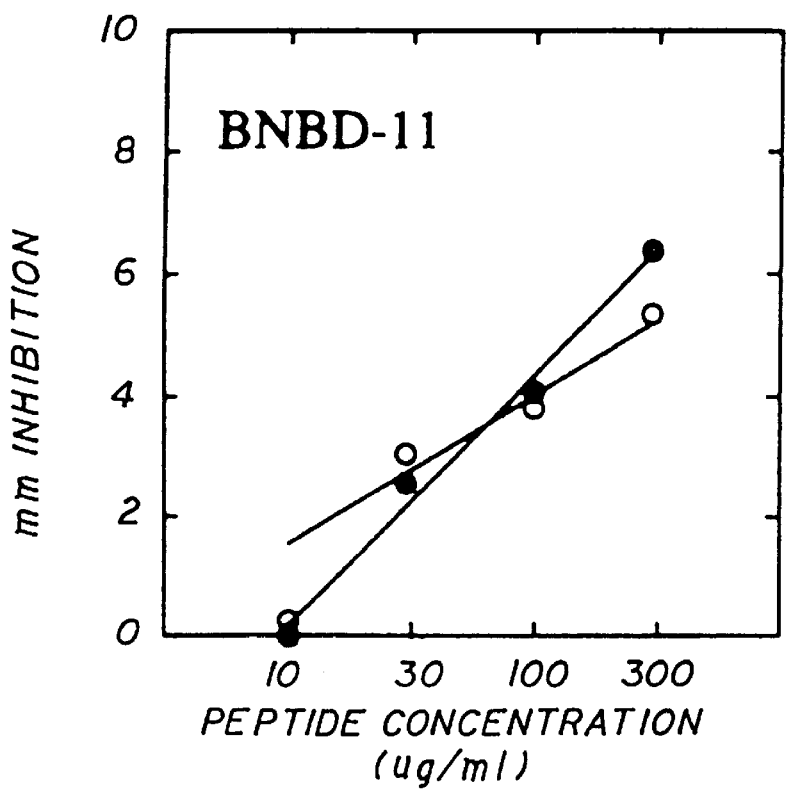
Figure 7L:
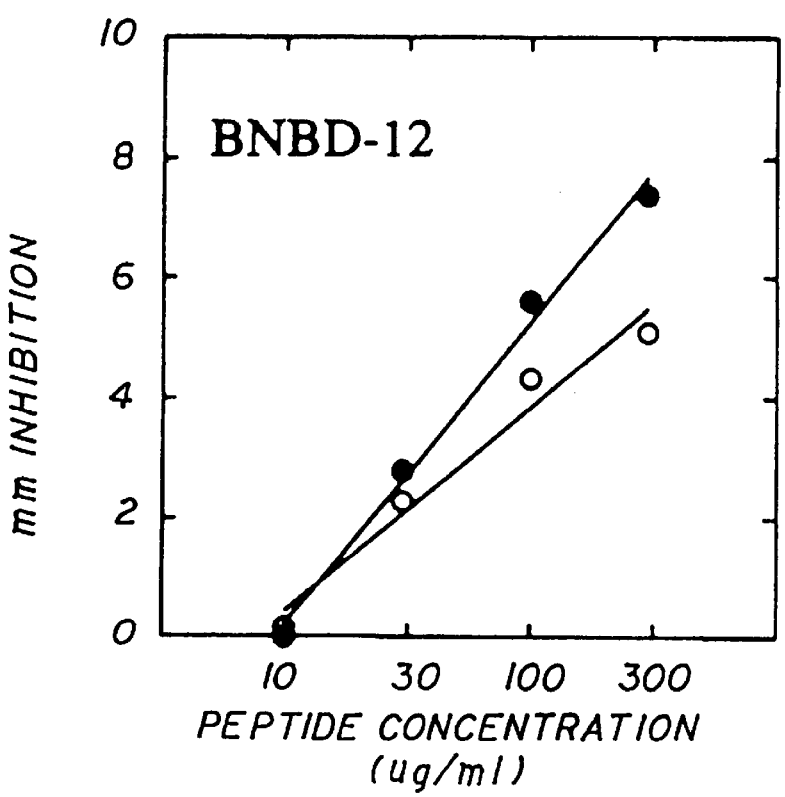
Figure 7M:
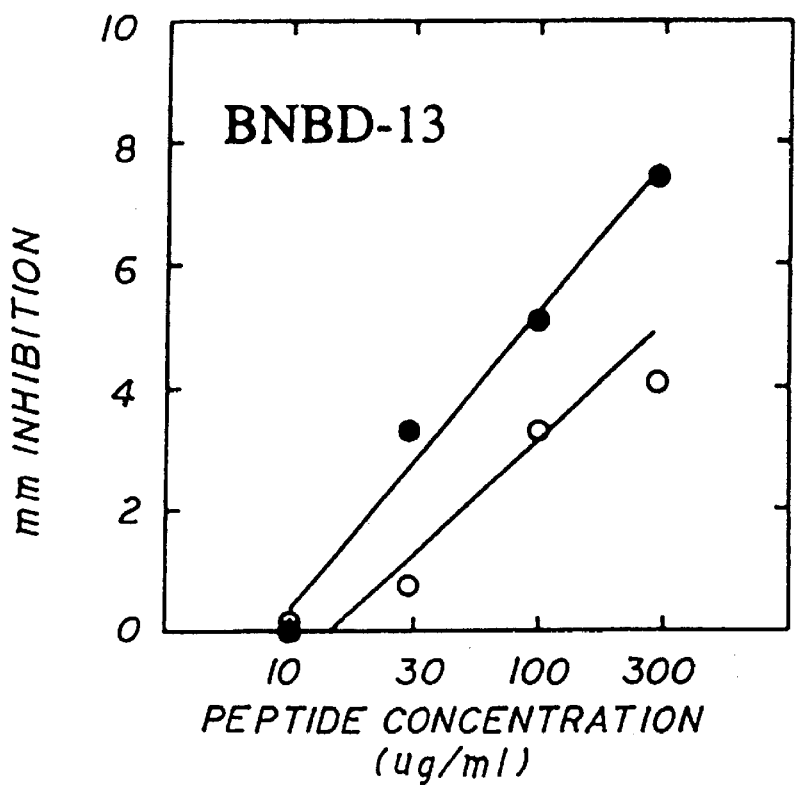
Figure 7N:
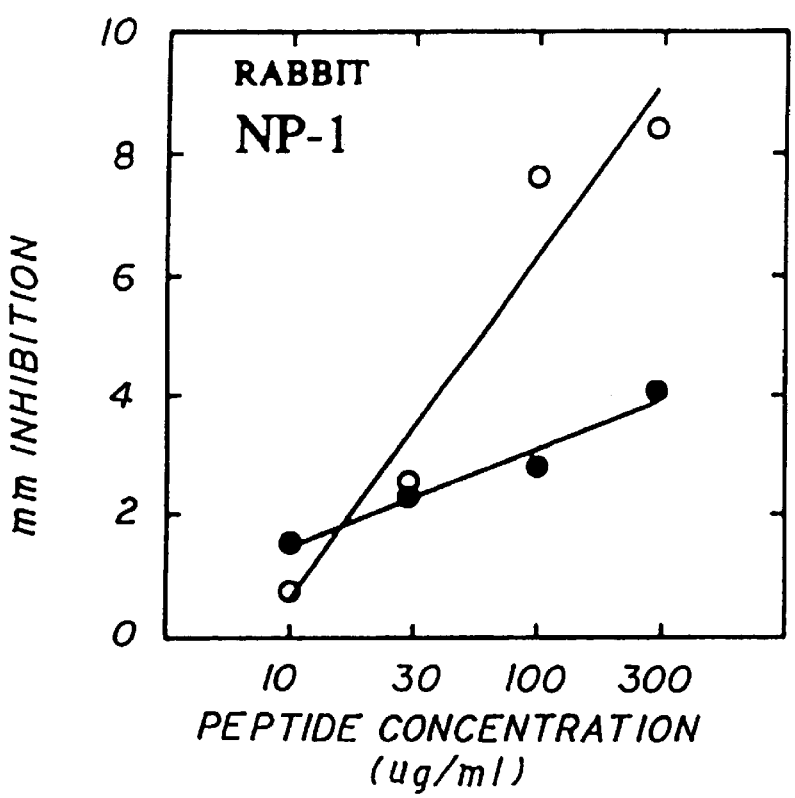
Figure 7O:
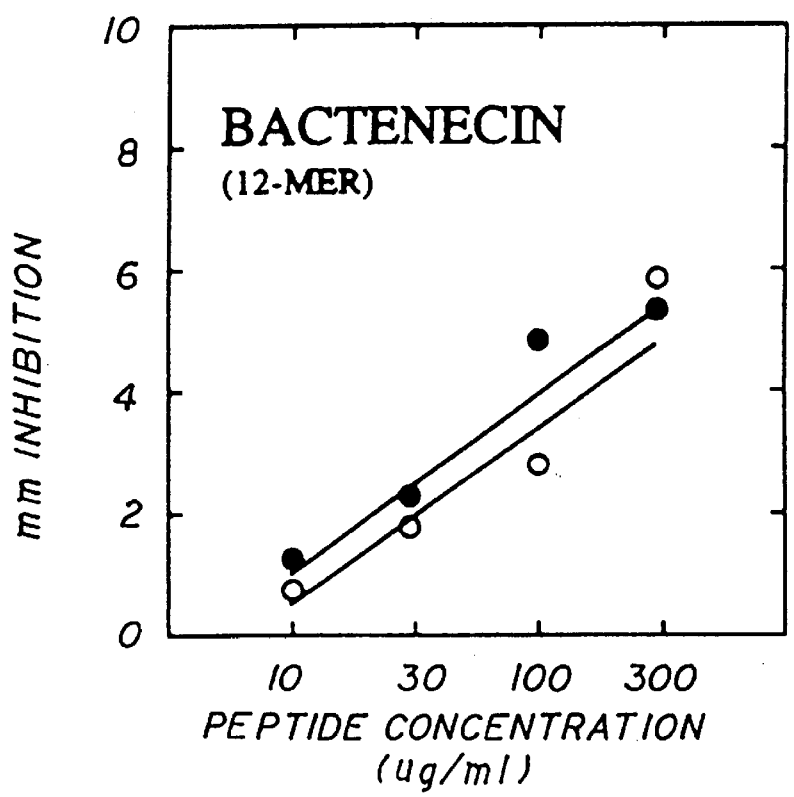
Figure 7P:
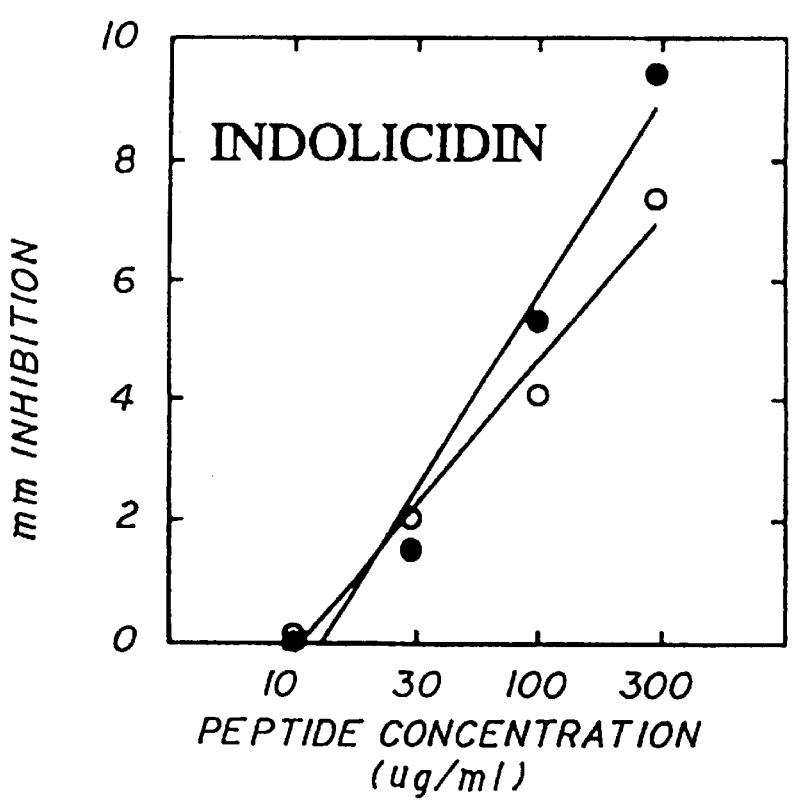

The initial RP-HPLC purification of Peak E fractions yielded a complex chromatogram (FIG. 2) in which most peaks contained two or more peptides as determined by acid-urea PAGE. One of the earliest peaks (indicated by in FIG. 2) contained an antibacterial peptide of ca. 1500 D. Automated sequence analysis (data not shown) revealed that this peptide was identical to the cyclic dodecapeptide bactenecin described earlier by Romeo et al. (*J. Biol. Chem.* 263:9573–9575 (1988)). Subsequent steps in the purification of the 13 peptides described here employed modified gradient conditions and/or use of 0.13% HFBA as the ion pairing agent. These steps enabled the purification of thirteen unique peptides, each of which was determined to be pure by its homogeneous behavior on analytical RP-HPLC (FIG. 3) and acid-urea PAGE (FIG. 4). As described below, the peptides constitute a family of related peptides [bovine neutrophil beta-defensins (BNBDs)] which have been numbered 1–13 based on their increasing retention times on RP-HPLC. (FIG. 3, Table I). Peptides eluting in unnumbered peaks in FIG. 2 were characterized by amino acid analysis and DSD-PAGE and were either devoid of cysteine or were much larger than BNBD 1–13, indicating that these peptides were unrelated to beta-defensins.

The cellular content of beta-defensin peptide was estimated by quantitating the amount of homogenous BNBD 1–13 recovered, and correcting for losses at each step in purification. Using acid-urea and SDS-PAGE to assess recovery, we estimated that ca. 80% of the cellular content of beta-defensins was extracted from granule enriched fractions, and that recovery from the P-60 column was virtually quantitative. Assuming 75% recovery during RP-HPLC, the quantity of the combined thirteen beta-defensins, averaged from two complete purifications, was approximately 4.9 mg per $10^{10}$ neutrophils. The most abundant beta-defensin was BNBD-3, present at approximately 2.2 mg per $10^{10}$ cells, and the quantity of each of the remaining peptides was similarly estimated as summarized in Table I.

Amino acid analysis. The composition of each peptide was established by amino acid analysis of native and performic acid-oxidized or S-carboxamidomethylated samples, and each was analyzed at least twice. Absorbance scans of each of the peptides were carried out between 300 and 200 nm, providing an accurate estimate of tyrosine and tryptophan content (Edelhoch, *Biochem.* 6:1948–1954 (1967)). As summarized in Table I, the thirteen peptides contained from 38 to 42 amino acids, six of which were half-cystine residues. The native peptides did not react with Ellman's reagent or iodoacetamide, indicating that the cysteines were most likely present as disulfides. In addition to their high cysteine content, the peptides were generally right in the basic amino acids arginine and lysine, but tyrosine and alanine were relatively uncommon.

TABLE I

Amino Acid Composition, RP-HPLC retention times, electrophoretic mobilities and cellular quantities of BNBD 1–13

| Residues | BNBD-1 | BNBD-2 | BNBD-3 | BNBD-4 | BNBD-5 | BNBD-6 | BNBD-7 | BNBD-8 | BNBD-9 | BNBD-10 | BNBD-11 | BNBD-12 | BNBD-13 |
|---|---|---|---|---|---|---|---|---|---|---|---|---|---|
| Cya[b] | 6.04(6) | 6.56(6) | 6.20(6) | 6.34(6) | 5.59(6) | 5.81(6) | 6.37(6) | 6.18(6) | 6.41(6) | 5.73(6) | 6.16(6) | 5.91(6) | 5.94(6) |
| Asp | 3.03(3) | 2.16(2) | 2.01(2) | 1.74(2) | 2.58(3) | 0.99(1) | 1.91(2) | 1.67(2) | 2.20(2) | 2.04(2) | 0.92(1) | 0.94(1) | 0.95(1) |
| Glu | 0.95(1) | 1.08(1) | 1.93(2) | 2.88(3) | 2.70(3) | 1.99(2) | 1.90(2) | 2.04(2) | 3.12(3) | 2.20(2) | 1.01(I) | 1.02(1) | 0.93(1) |
| Ser | 1.73(2) | 0.82(1) | 0.86(1) | 0.82(1) | 1.78(2) | | | | | 1.67(2) | 1.75(2) | 1.84(2) | 3.78(4) |
| Gly | 3.72(4) | 4.40(4) | 5.11(5) | 3.73(4) | 3.87(4) | 6.52(6) | 4.99(5) | 3.96(4) | 5.10(5) | 5.32(5) | 6.23(6) | 6.40(6) | 7.30(7) |
| His | 1.99(2) | 0.84(1) | 0.83(1) | | | 0.91(1) | 0.89(1) | 0.98(1) | 0.85(1) | | | | |
| Arg | 4.57(4) | 8.01(8) | 7.97(8) | 7.73(8) | 5.24(5) | 8.47(8) | 7.92(8) | 6.57(7) | 7.29(7) | 7.02(7) | 6.06(6) | 5.71(5) | 5.35(5) |
| Thr | 0.98(1) | 2.61(3) | 2.60(3) | 1.07(1) | 0.91(1) | 2.56(3) | 1.86(2) | 1.92(2) | 1.84(2) | 1.12(1) | 1.12(1) | 0.94(1) | 0.98(1) |
| Ala | 0.93(1) | | | | | | | | | 1.00(1) | | | |
| Pro | 2.76(3) | 2.82(3) | 2.73(3) | 3.80(4) | 4.70(5) | 3.08(3) | 2.94(3) | 2.90(3) | 3.05(3) | 2.16(2) | 5.04(5) | 4.86(5) | 5.05(5) |
| Tyr | | | | | | 0.93(1) | | | | 1.08(1) | | | |
| Val | 0.85(1) | 2.78(3) | 2.61(3) | 3.56(4) | 3.58(4) | 3.86(4) | 2.81(3) | 2.90(3) | 2.98(3) | 2.12(2) | 1.66(2) | 2.56(3) | 2.93(3) |
| Met | 0.72(1) | | | 1.45(2) | 2.13(2) | | | | | 1.23(1) | 1.03(1) | 0.93(1) | 0.89(1) |
| Ile | 3.19(4) | 3.65(4) | 3.64(4) | 1.83(2) | 3.01(3) | 3.06(3) | 3.82(4) | 3.70(4) | 3.84(4) | 2.00(2) | 2.91(3) | 3.01(3) | 4.03(4) |
| Leu | 1.07(1) | | | 1.00(1) | | | 1.00(1) | 1.19(1) | 1.39(1) | 4.09(4) | 1.06(1) | 1.13(1) | 1.07(1) |
| Phe | 2.00(2) | 2.00(2) | 2.00(2) | 1.82(2) | 1.00(1) | 2.10(2) | 1.92(2) | 1.86(2) | 1.85(2) | | 1.00(1) | 1.18(1) | 1.00(1) |
| Lys | 0.90(1) | 0.79(1) | 0.74(1) | | | 1.00(1) | 0.99(1) | 1.00(1) | 1.00(1) | 1.00(1) | 0.75(1) | 1.00(1) | 0.91(1) |
| Trp | (1)[c] | (1)[c] | (1)[c] | (1)[d] | (1)[d] | (1)[c] | | | | (1)[d] | (1)[c] | (1)[c] | (1)[c] |
| Total | 38 | 40 | 42 | 41 | 40 | 42 | 40 | 38 | 40 | 40 | 38 | 38 | 42 |
| MW[f] | 4273 | 4643 | 4009 | 4760 | 4443 | 4816 | 4550 | 4354 | 4522 | 4504 | 4158 | 4101 | 4445 |

TABLE I-continued

Amino Acid Composition, RP-HPLC retention times, electrophoretic mobilities and cellular quantities of BNBD 1–13

| Residues | BNBD-1 | BNBD-2 | BNBD-3 | BNBD-4 | BNBD-5 | BNBD-6 | BNBD-7 | BNBD-8 | BNBD-9 | BNBD-10 | BNBD-11 | BNBD-12 | BNBD-13 |
|---|---|---|---|---|---|---|---|---|---|---|---|---|---|
| HPLC RT (min)[g] | 18.25 | 18.32 | 18.32 | 19.99 | 20.03 | 20.81 | 20.87 | 21.72 | 21.94 | 22.30 | 22.72 | 24.30 | 24.83 |
| AU-PAGE (order)[h] | 9 | 3 | 4 | 8 | 13 | 6 | 1 | 2 | 5 | 10 | 7 | 11 | 12 |
| mg/$10^{10}$ cells[i] | 0.10 | 0.27 | 2.17 | 0.17 | 0.06 | 0.25 | 0.12 | 0.17 | 0.15 | 0.43 | 0.27 | 0.70 | 0.06 |

[d]Values determined from vapor phase HCl hydrolysis as described in experimental procedures. Numbers in parentheses indicate residues determined by sequence analysis.
[b]Cya (cysteic acid) analyzed after performic acid oxidation.
[c]Tryptophanyl residues identified by U.V. spectrophotometry and release by carboxypeptidase A.
[d]Tryptophanyl residues identified by U.V. spectrophotometry and also determined by automated Edman degradation.
[e]Tryptophanyl residues identified by U.V. spectrophotometry, by release with carboxypeptidase Y treatment, and confirmed by mass spectrometry.
[f]Molecular weights calculated from amino acid sequences (FIG. 5).
[g]HPLC retention time (see FIG. 3 for HPLC conditions).
[h]Relative order of migration on acid urea-PAGE with 1 being the highest $R_f$ and 13 the lowest $R_f$ value (see FIG. 4).
[i]Approximate content of each peptide based on recovery as described under results.

Sequence analyses. Two cycles of manual Edman degradation allowed the identification of N-terminal residues of six peptides (BNBDs 1,2,8,11,12, & 13). The N-termini of the remaining seven peptides were deblocked with pyroglutamate aminopeptidase, demonstrating the presence of a pyroglutamyl residue at the N-terminus of each of these peptides. Automated sequence analysis was carried out on 1 to 5 nmol of each S-alkylated peptide. Repetitive sequencing yields averaged 93 to 97 percent, allowing for unambiguous assignment of 511 of 519 amino acids by automated Edman degradation. The eight residues requiring additional steps for identification included the carboxyl terminal tryptophan of BNBDs 1, 2, 3, 6, 11, 12, and 13, and the carboxyl terminal arginine of BNBD-4. With the exceptions of BNBD-4 and -6, the carboxyl terminus of each of the eight above mentioned peptides was determined by analysis of carboxypeptidase A-released amino acids. The carboxyl terminal arginine of BNBD-4 was confirmed by amino acid analysis of a purified chymotryptic peptide composed of residues 33 to 41 which had the composition Gly (1.27), Arg (2.64), Pro (2.06), Val (0.98), Cys (1.59). The overall composition of this fragment and its content of (3) arginine residues are consistent with the presence of the Arg-Arg dipeptide at the carboxyl terminus.

The tryptophan assigned as the carboxyl terminus of BNBD-6 was released poorly by carboxypeptidases A and Y. To confirm the C-terminal tryptophan, the mass of BNBD-6 was determined on a sample of native peptide by fast atom bombardment mass spectrometry. The monoisotopic mass of BNBD-6 was 4814.2 amu, in close agreement with the theoretical mass of 4816, and consistent with the presence of the C-terminal tryptophan. Further, ultraviolet spectral analysis (Endelhoch Id.) indicated the presence of a single tryptophan in both the intact peptide and in the carboxyl-terminal chymotryptic fragment containing residues 33–42. The sequences of all thirteen peptides were in excellent agreement with their respective amino acid compositions (Table I).

The complete amino acid sequences of BNBD 1–13, shown in FIG. 5, reveal the high degree of primary structural similarity of this peptide family. Like defensins, each peptide is characterized by six invariant cysteine residues, two of which are sequential and situated near the peptide carboxyl terminus. However, the spacing of the other cysteine residues in the sequence differs from defensins, and the disulfide connectivities, determined in BNBD-12, differ from those of defensins (Selsted et al., *J. Biol. Chem.* (1992) (submitted)).

In addition to the conserved cysteines, the beta-defensin sequences contain several amino acids that are highly if not absolutely conserved (FIG. 5). By aligning highly conservative substitutions (Ser/Thr; Val/Ile/Leu/Phe) and one position where only Pro or Arg appears in the primary structures of 10 or more beta-defensins, a common consensus sequence of 27 amino acids is revealed (FIG. 6).

A sequence similarity search using the BLAST algorithm (Altschul et al., *J. Mol. Biol.* 215:403–410 (1990)) revealed only a single protein with substantial identity to the beta-defensins, this being tracheal antimicrobial peptide (TAP), a peptide isolated by Diamond et al. from bovine tracheal epithelium (Diamond et al., *Proc. Natl. Acad. Sci. USA* 88:3952–3956 (1991)). The primary structure of TAP contains the 27-residue beta-defensin consensus sequence, though it is not identical to any of the neutrophil-derived beta-defensins described here (FIG. 6).

Antimicrobial activity of beta-defensins. The antibacterial activity of each beta-defensin was evaluated using *Staphylococcus aureus* 502A and *Escherichia coil* ML35 as test organisms. Using a sensitive radial diffusion assay, each peptide was tested against the two bacterial organisms with beta-defensin concentrations ranging from 10 to 300 µg/ml. The data presented in FIG. 7 reveal the dose-dependent activity of each peptide as measured by the size of the clear zone surrounding the sample well. In most cases, the log of the peptide concentration was linearly related to the diameter of the growth-free zone. Though the relative potencies of peptides differed, all thirteen were active against *E. coli*, and all but BNBD-1 and BNBD-5 were active against *S. aureus* in the range of concentrations tested. In most cases, the zone of clearing was greater against *E. coli* than *S. aureus*.

The antibacterial activities of the beta-defensins were compared with those of three previously characterized antimicrobial peptides: rabbit neutrophil defensin NP-1, the most potent of the classical defensins, indolicidin, and the cyclic dodecapeptide bactenecin. Like the beta-defensins, the latter two peptides were purified from bovine neutrophil granules. As shown in FIG. 7, the anti-staphylococcal activity of rabbit NP-1 was the greatest of any of the peptides tested, though the activity of NP-1 against *E. coli* was modest when compared to nearly all of the beta-defensins. The potency of the dodecapeptide bactenecin was similar to that of several of the beta-defensins against both bacteria, but less so than the most active beta-defensins (e.g., BNBD's 7, 9, 12, and 13.) On a mass basis, indolicidin was the most active peptide against *E. coli*, and it was nearly as active as rabbit NP-1 against *S. aureus*.

EXAMPLE III

Material and Methods

BNBD-12 purification. BNBD-12 was purified to homogeneity as described (Selsted et al., *J. Biol. Chem.* (submitted)).

Chemicals. Sequence grade pyridine, phenylisothiocyanate (PITC), trifluoroacetic acid (TFA), heptane, ethyl acetate, and HCl were purchased from Pierce Chemical Co. Sequence grade n-butyl acetate from Aldrich. Hydrogen peroxide (30%), formic acid (90%) and HPLC grade water and acetonitrile were from Fisher. Tosylamide-2-phenylethyl chloromethyl ketone (TPCK)-treated trypsin was from Worthington.

Tryptic digestion. BNBD-12 (15 nmol was digested for 4 or 24 h at 37° C. with 8 μg of TPCK-trypsin in 50 μl of 0.1M pyridine acetate, pH 6.48. The reaction was terminated by acidification with TFA, and the mixture was taken to dryness in a Speed Vac evaporator (Savant).

Reversed Phase (RP) HPLC. Tryptic fragments were purified by RP-HPLC on a Waters 510 binary gradient system. Samples were applied to a 4.6×250 mm Vydac C-18 column developed with gradients of water and acetonitrile containing 0.1% TFA. Details of individual chromatographic runs are provided in the legends to figures.

Amino acid analysis. Samples were performic acid oxidized prior to amino acid analysis. Lyophilized peptide sample (2 nmol) was dissolved in 50 μl of freshly prepared performic acid and incubated for 30 minutes at room temperature. To remove performic acid, the solution was diluted with 50 μl of HPLC grade water and lyophilized, and this was then repeated twice. Samples were hydrolyzed in vacuo at 110° for 24 or 48 hours in the gas phase of 6.0M HCl containing 1% phenol. Amino acid compositions were determined following derivitization with PITC (Bidlingmeyer et al., *J. Chromatogr.* 336:93–104 (1984)).

Manual Edman degradation. The procedure for manual Edman degradation was essentially that described by Klemm (Methods in Molecular Biology pp. 243–254 (Human Press 1984)). After the n-butyl acetate extraction step, both the organic and aqueous phases were dried under vacuum, dissolved in 50 μl of 1.0M HCl and converted to the phenylthiohydantoin (PTH) derivatives at 80° C. for 10 minutes. The aqueous phase, containing peptides liberated by Edman degradation, was subjected to RP-HPLC. The organic phase was analyzed by RP-HPLC (Klemm, supra) for identification of the released PTH-amino acid.

EXAMPLE IV

Results

Proteolytic digestion. The strategy used for establishing the cysteine pairing in BNBD-12 is summarized schematically in FIG. 8. Note that residue numbering is indexed to the longest of the beta-defensins (Selsted et al., *J. Biol. Chem.* (submitted)). Inspection of the sequence indicated that digestion of BNBD-12 with trypsin would yield several proteolytic fragments, characterization of which would permit the assignment of the disulfide bonds. To reduce the possibility of disulfide shuffling, digestion with trypsin was performed at pH$\leq$6.48.

Figure 8A:
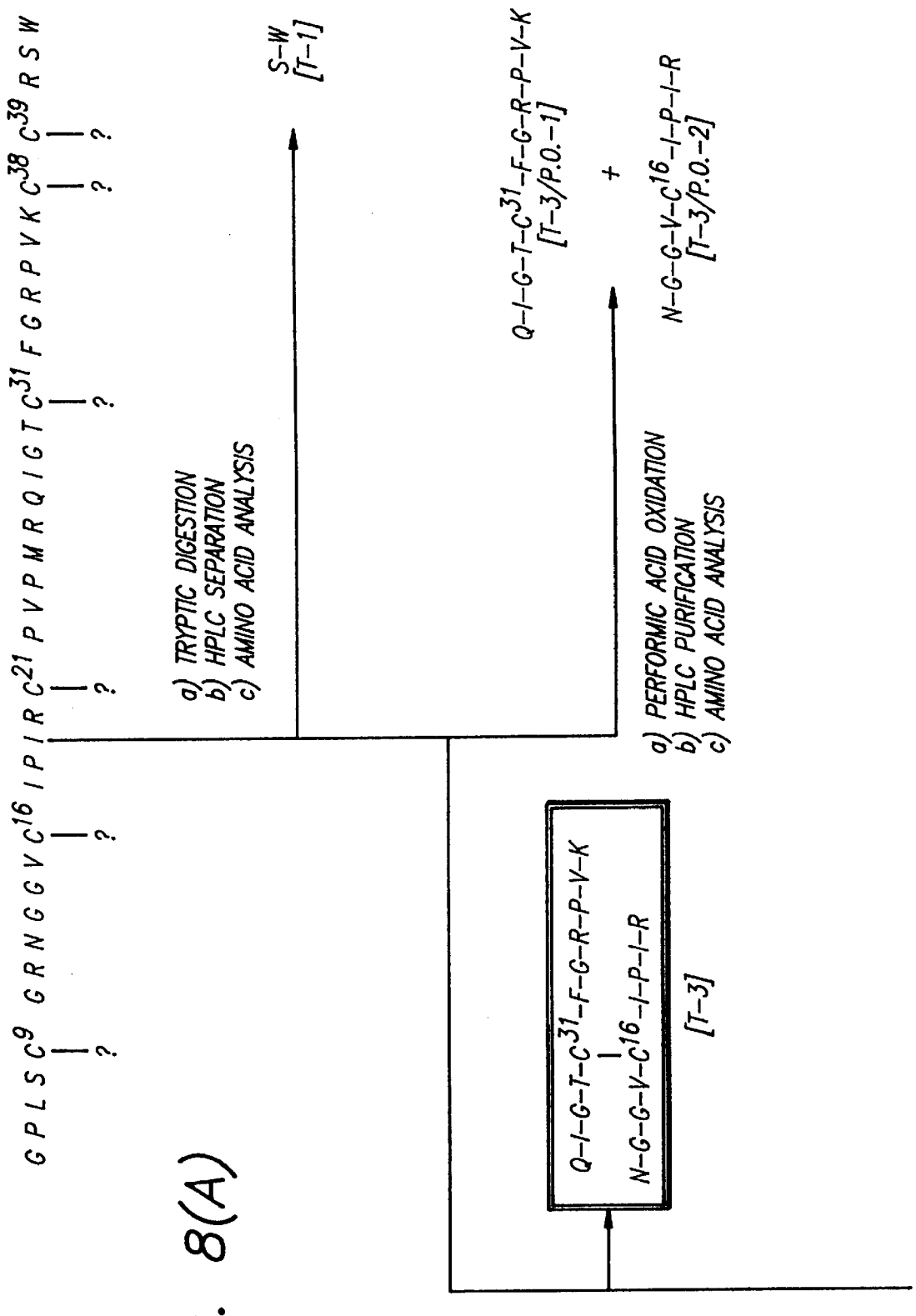
FIG. 8. Strategy for determination of the disulfide bonding pattern in BNBD-12. Native BNBD-12 (SEQ ID NO: 16) was subjected to digestion with trypsin as described in Materials and Methods. Fragments (identified by bracketed nomenclature) (SEQ ID NOS: 17–20) were purified by RP-HPLC (FIGS. 9–11) and characterized. Alternative structures of T-2 are enclosed in the single lined box. Fragments outlined with double lines contain disulfides present in native BNBD-12 (bottom of figure).
Figure 8B:
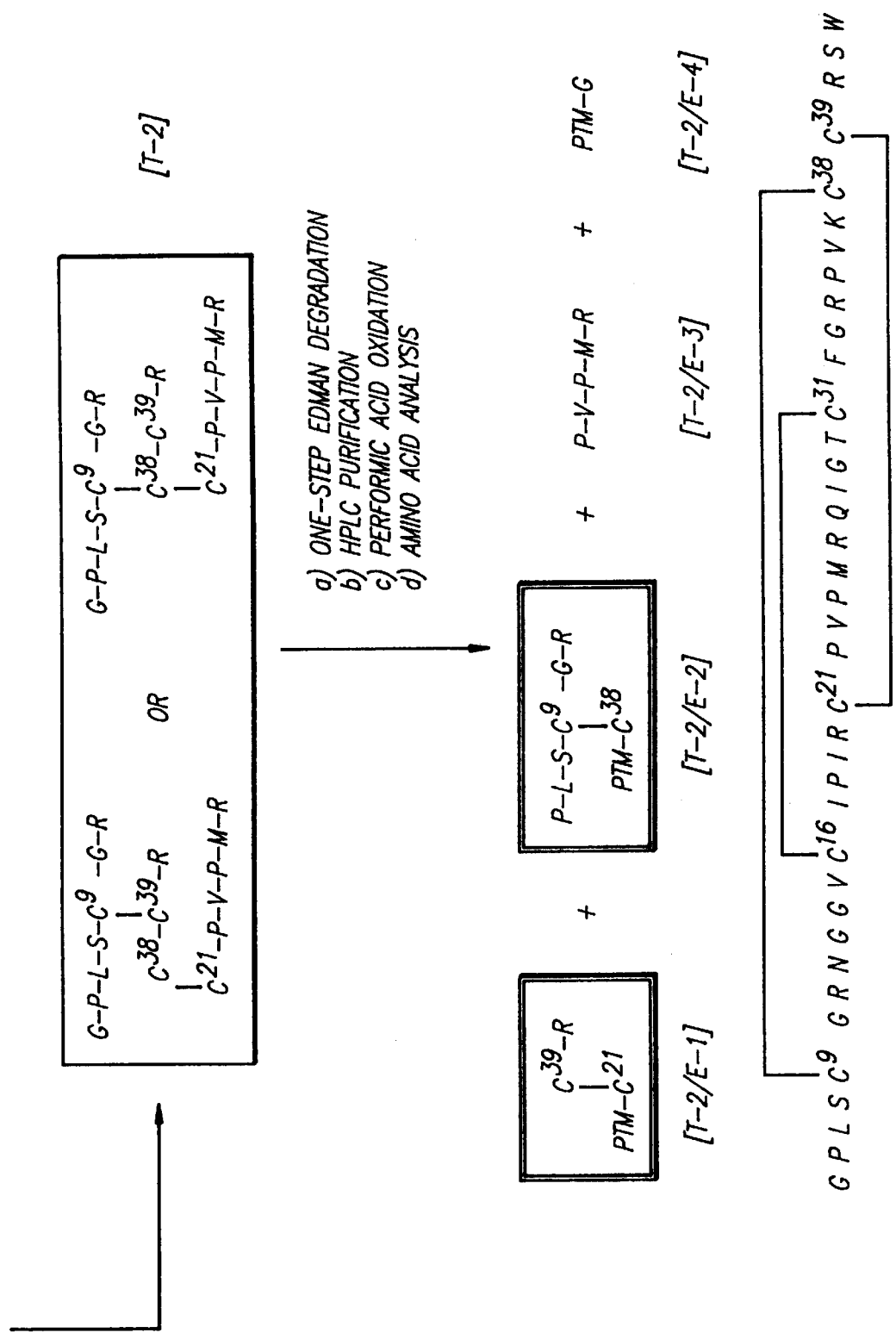
Figure 9:
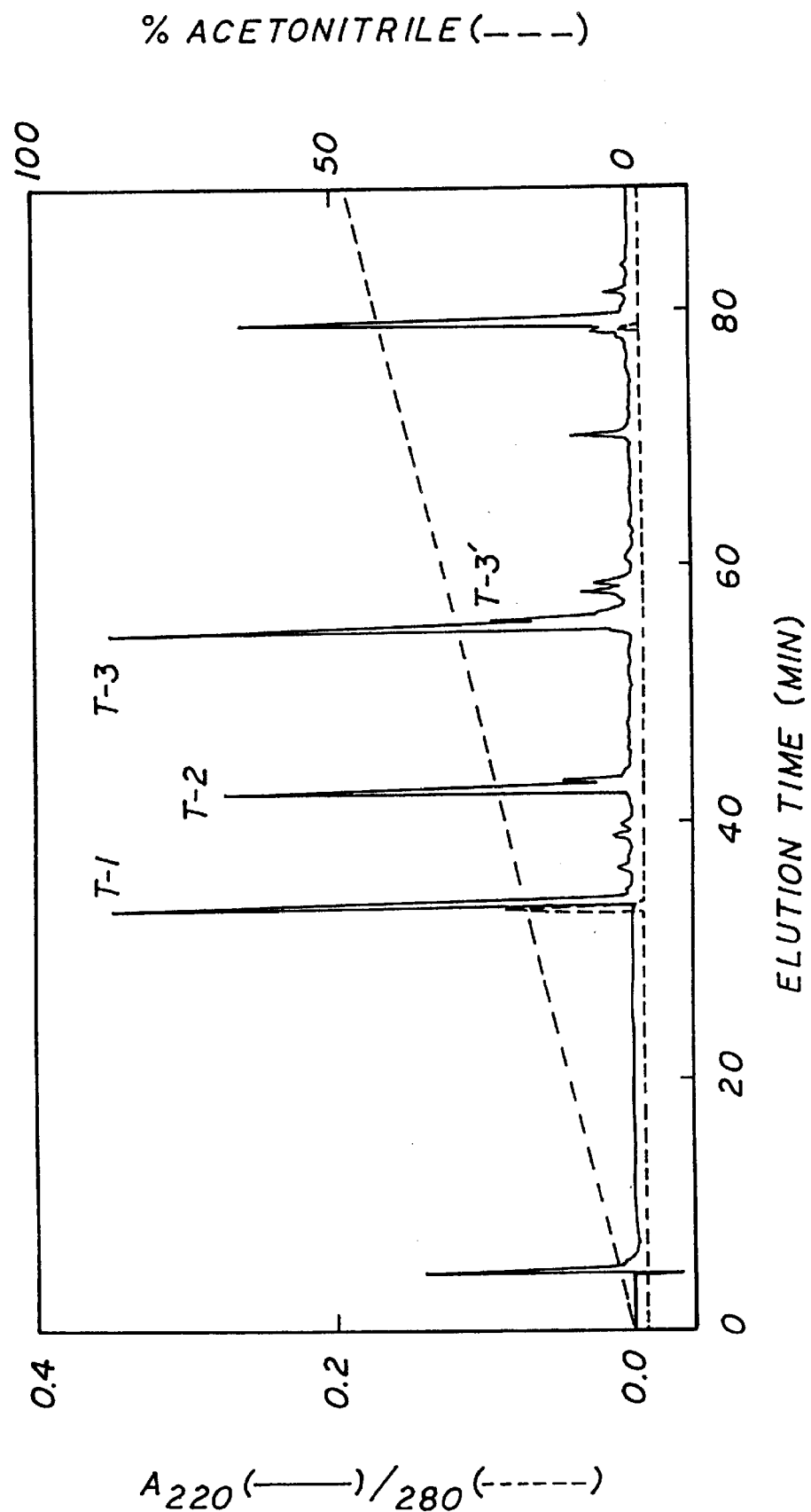
FIG. 9. RP-HPLC of the tryptic digest of native BNBD-12. Approximately 7.5 nmol of trypsin-digested BNBD-12 was purified by gradient elution on a Vydac C-18 column. Flow rate was 0.1 ml per min; solvent A was 0.1% TFA in water, solvent B was 0.1% TFA in acetonitrile. Gradient conditions: 0–40% (80 minutes). The major tryptic fragments are labelled T-1, T-2, and T-3. The peak eluting at 80 minutes was determined to be undigested BNBD-12. The peak labelled T-3' was characterized by amino acid analysis and determined to be a des-Pro-Val-Lys T-3 fragment.

Fifteen nmol of BNBD-12 was digested with TPCK-trypsin for 4 hours, and half of the digest was purified by RP-HPLC (FIG. 9). The latest eluting peak (ca. 80 minutes) was determined by its retention time and amino acid composition to be undigested BNBD-12. The amino acid compositions of the three tryptic fragments (T-1, T-2, and T-3) were determined, and allowed for their placement within the primary sequence (FIG. 8). The C-terminal Ser-Trp dipeptide (T-1) which eluted at 30 minutes was readily identified by its serine content on amino acid analysis, its $A_{280}$ absorbance (FIG. 9), and the classical tryptophanyl UV signature determined by spectral scanning (data not shown; (Edelhoch, *Biochem.* 6:1948–1954 (1967)).

Figure 10:
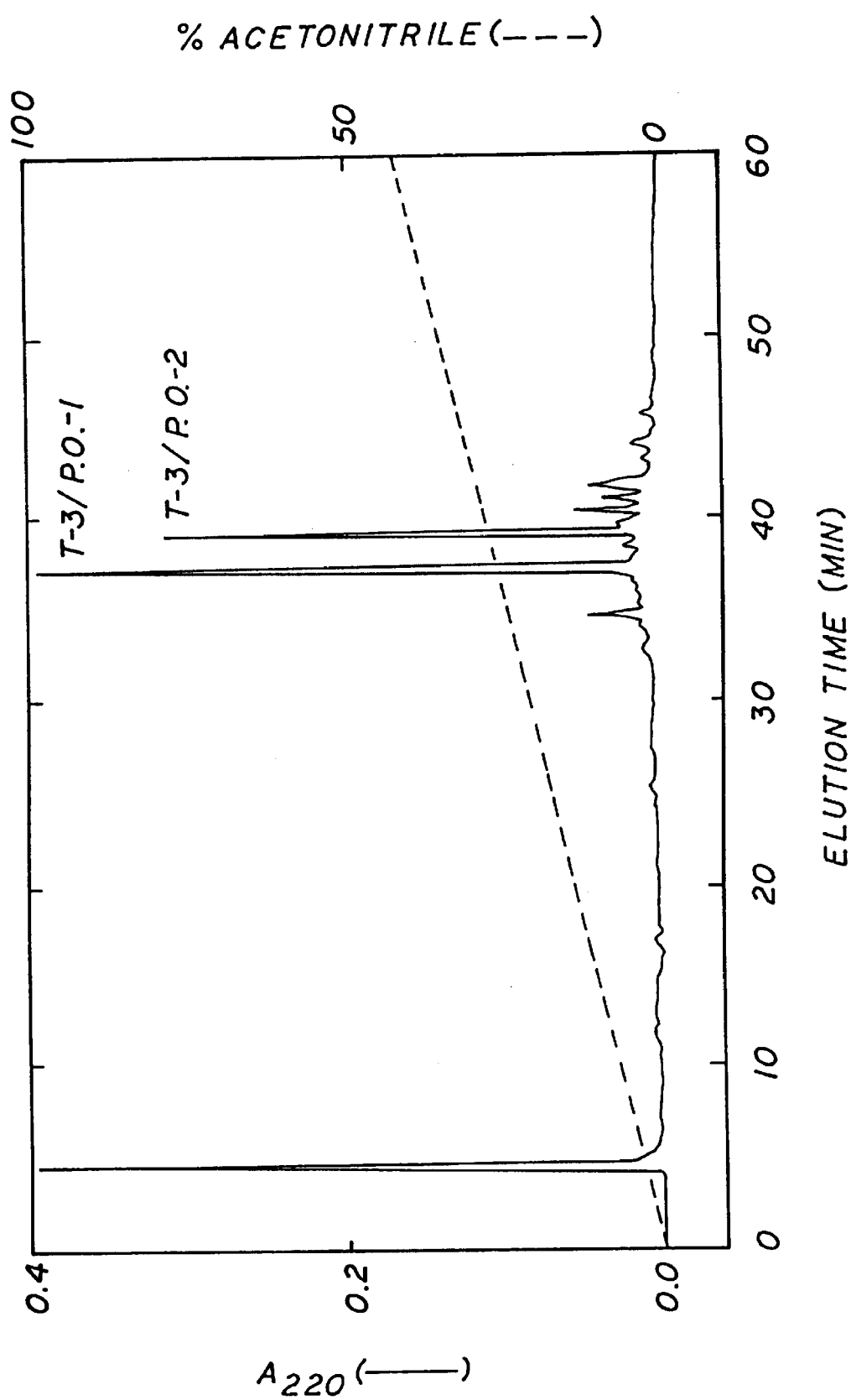
FIG. 10. RP-HPLC purification of the products of performic acid-oxidation of tryptic peptide T-3. Six nmol of T-3 was treated with performic acid and the reaction products were purified on a Vydac C-18 column. Solvents and flow rates were as in FIG. 9. Gradient conditions: 0–40% B (60 minutes).

The amino acid composition of fragment T-3 revealed that it contained a single pair of disulfide-linked cysteines (Table II). Comparison of the amino acid content with the primary sequence permitted the assignment of the $Cys^{16}$-$Cys^{31}$ disulfide in BNBD-12 (FIG. 8). Additional confirmation was obtained by analyzing the constituent disulfide-linked oligopeptides. A 6 nmol sample of T-3 was performic acid-oxidized, and the two resulting cysteic acid-containing peptides (T-3/P.O.-1 and T-3/P.O.-2) were purified by RP-HPLC (FIG. 10) and characterized by amino acid analysis. As summarized in Table II and FIG. 8, the compositions of T-3/P.O.-1 and T-3/P.O.-2 were in complete agreement with the $Cys^{16}$-$Cys^{31}$ disulfide assignment.

TABLE II

Amino Acid Compositions of Tryptic and Edman Degradation Fragments of BNBD-12[a]

| | | | Residues in Peptides | | | | |
|---|---|---|---|---|---|---|---|
| Amino Acid | T-1[b] | T-2 | T-3 | T-2/E-1 | T-2/E-2 | T-2/E-3 | T-3/P.O.-1 | T-3/P.O.-2 |
| Cya | | 3.16(4) | 1.60(2) | 0.83(1) | 0.80(1) | | 1.01(1) | 0.71(1) |
| Asp | | | 1.16(1) | | | | | 1.00(1) |
| Gly | | | 0.94(1) | | | | 1.09(1) | |
| Ser | (1) | 1.20(1) | | | 0.72(1) | | | |
| Gly | | 2.60(2) | 4.20(4) | | 1.16(1) | | 2.30(2) | 2.45(2) |
| Arg | | 3.01(3) | 1.97(2) | 1.00(1) | 1.00(1) | 0.97(1) | 1.34(1) | 1.13(1) |
| Thr | | | 1.21(1) | | | | 0.94(1) | |
| Pro | | 2.91(3) | 1.54(2) | | 1.09(1) | 2.04(2) | 0.93(1) | 0.79(1) |
| Val | | 1.12(1) | 1.31(1) | | | 1.00(1) | 0.84(1) | 0.77(1) |
| Met(0) | | N.D.[c] | | | | N.D.[c] | | |
| Ile | | | 2.18(3) | | | | 1.00(1) | 2.05(2) |
| Leu | | 1.01(1) | | | 0.65(1) | | | |
| Phe | | | 1.00(1) | | | | 1.27(1) | |
| Trp | (1) | | | | | | | |

TABLE II-continued

Amino Acid Compositions of Tryptic and Edman Degradation Fragments of BNBD-12[a]

| Amino Acid | T-1[b] | T-2 | T-3 | T-2/E-1 | T-2/E-2 | T-2/E-3 | T-3/P.O.-1 | T-3/P.O.-2 |
|---|---|---|---|---|---|---|---|---|
| Lys | | 0.51(1) | | | | | 0.94(1) | |

[a] Samples were hydrolyzed for 24 or 48 hrs after performic acid oxidation; numbers in parentheses refer to residues in the BNBD-12 sequence; fragment nomenclature refers to that shown in FIG. 1.
[b] Only serine detected after hydrolysis; tryptophan was determined spectrophotometrically.
[c] N.D., Not Detected.

Figure 11:
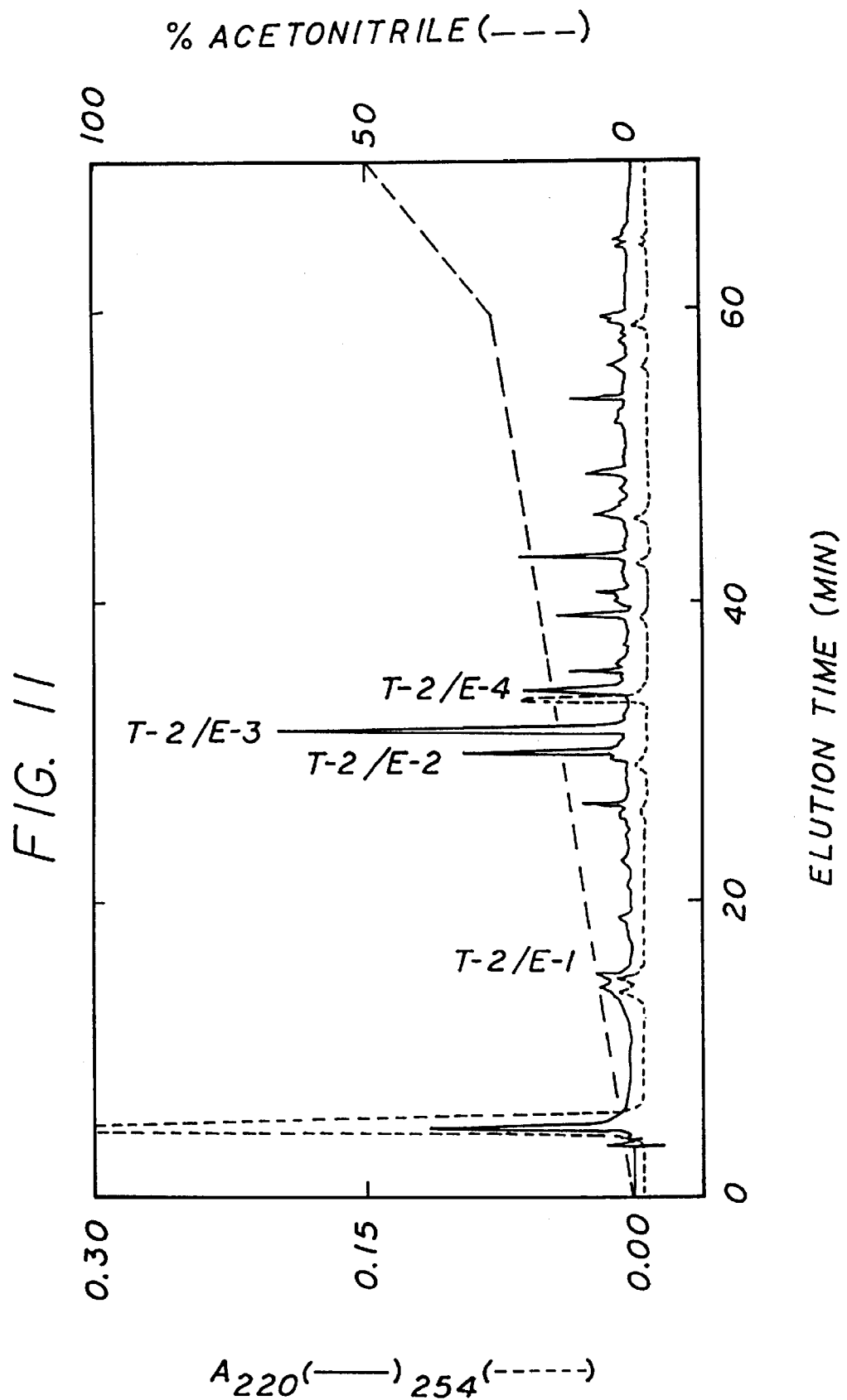
FIG. 11. RP-HPLC of the products of Edman degradation of tryptic peptide T-2. Following a single step of Edman degradation, the aqueous phase products were separated on a Vydac C-18 column. Solvents and flow rates were as in FIG. 9. Gradient conditions: 0–25% B (60 minutes), 25%–50% B (10 minutes).
Figure 12A:
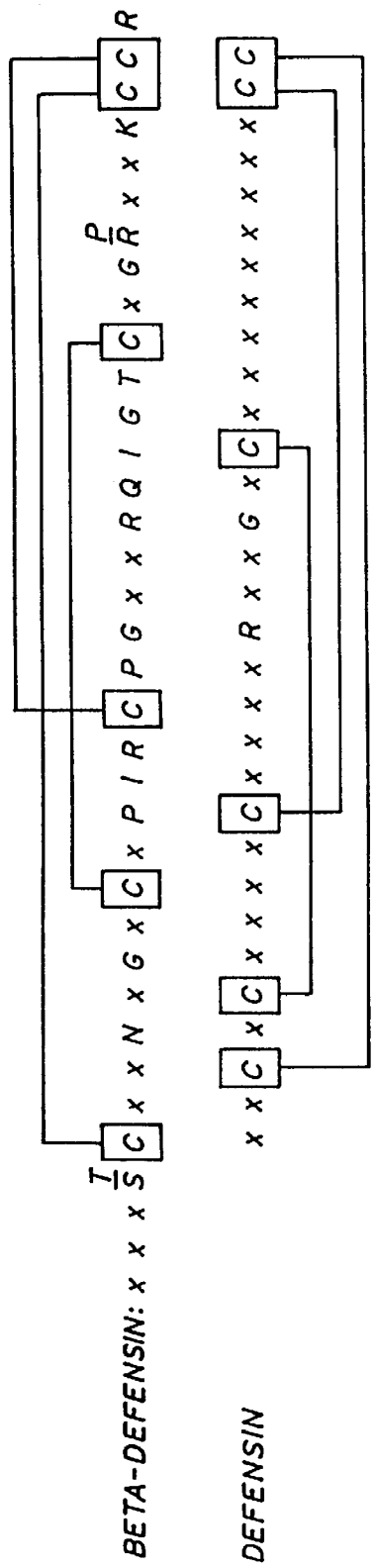
FIGS. 12A & B. Comparison of beta-defensin and defensin covalent structures. Consensus sequences for defensins (SEQ ID NO: 22) and beta-defensins (SEQ ID NO: 21) are shown in a single amino acid code. TIS and P/R are shown in positions in the beta-defensin consensus where only two alternate residues appear. Cysteine connectivities are shown as solid lines.
Figure 12B:
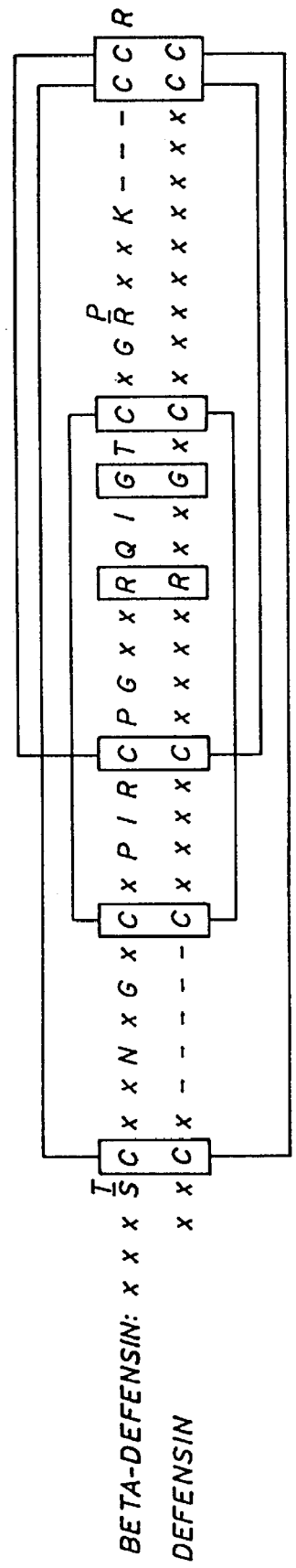
FIG. 12B. Maximized alignment generated by insertion of a 3 residue gap near the carboxyl terminus of the beta-defensin consensus, and a 5 residue gap near the amino terminus of the defensin consensus.

The amino acid composition of T-2 showed it to be a 16-amino acid oligopeptide containing four cysteic acids (Table II), demonstrating that this tryptic fragment contained the two remaining disulfides. Comparison of the T-2 composition with the BNBD-12 sequence revealed two possible configurations linking the four unassigned cysteines in the peptide chain. The two possible structures of this oligopeptide, enclosed by the single-line box in FIG. 8, differ only in the disulfide connectivities of the 4 cysteine residues. To distinguish between the alternative bonding patterns, it was necessary to cleave the $Cys^{38}$-$Cys^{39}$ peptide bond so that the resulting pair of disulfide-containing peptides could be characterized. This was achieved by subjecting a 10 nmol sample of T-2 to a single cycle of manual Edman degradation. After the cleavage step and acid conversion to the PTH derivative, the aqueous phase of the reaction mixture was separated by RP-HPLC (FIG. 11). Amino acid analysis revealed that one of the HPLC-purified reaction products (T-2/E-2) contained 1 Cya, 1 Ser, 1 Gly, 1 Arg, 1 Pro, and 1 Leu; PTH-Cya was not recovered under these conditions. Release of this product indicated that the structure of T-2 is that shown on the right of the single lined box in FIG. 8. If the alternative structure were correct, amino acid analysis of T-2/E-2 would reveal 2 rather than 1 arginine. The structure of T-2 was further confirmed by the characterization of the other products of the Edman degradation step, all of which had the expected compositions: a) T-2/E-1 contained 1 Arg and 1 Cys; the PTH-Cys was not recovered in amino acid analysis; b) T-2/E-3 contained the expected 2 Pro, 1 Val and 1 Arg; methionine was destroyed by performic acid oxidation; c) T-2/E-4 was shown to be PTH-Gly on the RP-HPLC system for analysis of PTH amino acids (Klemm, Id.); further, analysis of the organic phase of the Edman degradation reaction mixture showed that ca. 80% of the PTH-Gly was extracted into this phase, and no other PTH amino acids were detected. A number of minor peaks, eluting between 20 and 50 minutes (FIG. 11) had compositions similar to T-2/E-2. These probably represent oxidation products generated during the Edman degradation reaction or in subsequent sample processing steps.

Taken together, the data presented demonstrate that the cysteine connectivities in BNBD-12 are $Cys^9$-$Cys^{38}$-$Cys^{16}$-$Cys^{31}$- and $Cys^{21}$-$Cys^{39}$ (FIG. 8). As with other cysteine-rich protein families, the disulfide motif described for BNBD-12 is almost certain to be conserved among all of the beta-defensins.

EXAMPLE V

Bactericidal Activities of Beta-Defensins

A 1:500 dilution of overnight cultures of *E. coli* ML35 and *S. aureus* 502A was incubated with shaking for 2.5 to 3 hours at 37° C. in trypticase soy broth (TSB). The bacteria were centrifuged at 10,000 rpm for 10 minutes at 4 c, washed with cold 10 mM sodium phosphate buffer, pH 7.4 and resuspended in cold phosphate buffer to a concentration of $1 \times 10^7$ cells/ml. Solutions of various concentrations of BNBDs were made up in 10 mM sodium phosphate buffer, pH 7.4. The bactericidal assay mixture contained 30 μl of the phosphate buffer, 10 μl ($1 \times 10^5$ cells) of the bacterial stock solution, and 10 μl of peptide giving final peptide concentrations of 0 to 50 μg/ml. Incubations were carried out at 37° C. for 30 minutes, after which a 30 μl aliquot was removed and diluted 10, 100, and 1000-fold. Duplicate 100 μl samples of each dilution were spread into TSB plates and incubated for 18 hours at 37° C. Colonies were counted with the Darkfield Colony Counter (Quebec).

Figure 13:
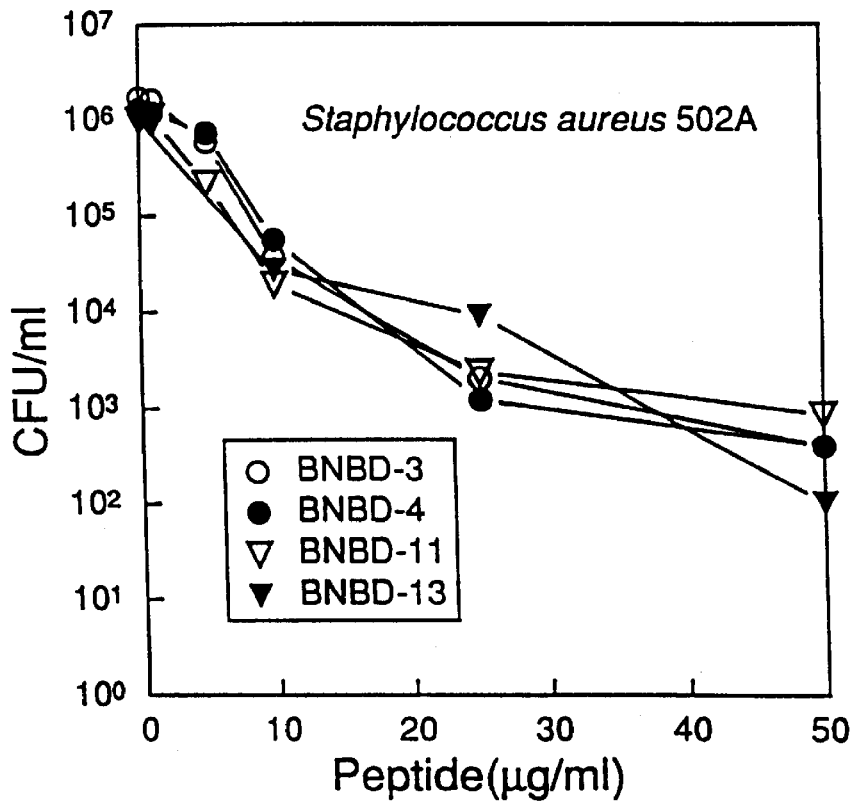
FIG. 13 shows the bactericidal activity of BNBD 3, 4, 11, and 13 against *S. aureas*.
Figure 14:
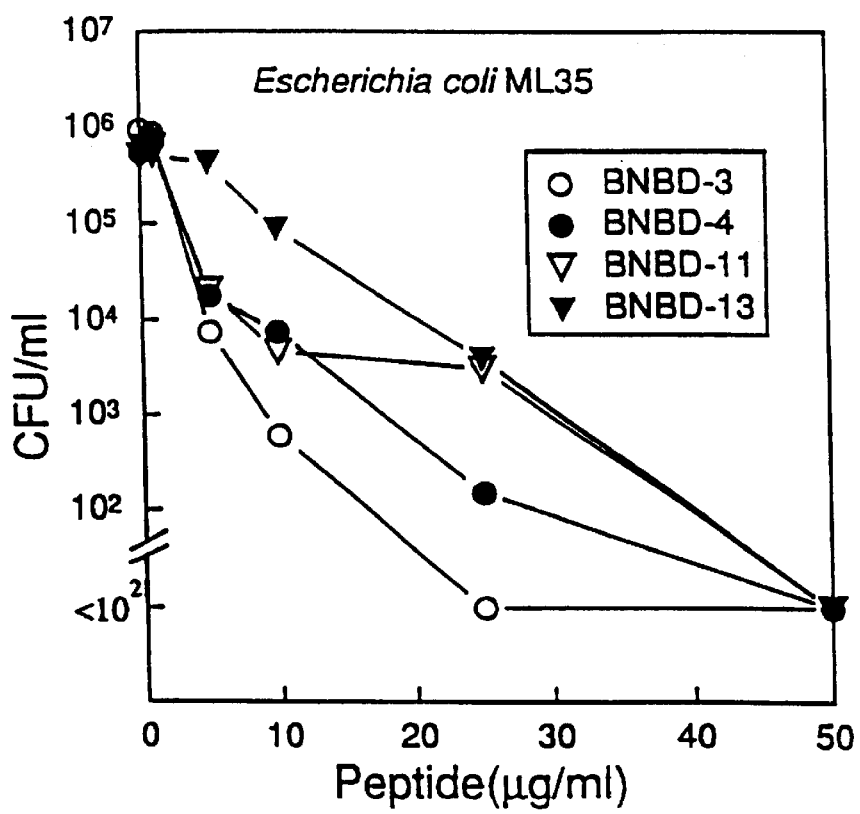
FIG. 14 shows the bactericidal activity of BNBD 3, 4, 11, and 13 against *E. coli*.

The accompanying figures shows that 5–0 μg/ml of each of four representative beta-defensins were equally effective against *S. aureus*, killing ca. 99.9% of the input organisms in 30 minutes (FIG. 13). At 50 μg/ml, the *E. coli* suspensions were essentially sterilized, though the potency of BNBD-3 was the greatest at lower concentrations (FIG. 14).

EXAMPLE VI

Fungicidal Activities of Beta-Defensins

*Candida albicans* 16820 and *Cryptococcus neoformans* 271A were grown with shaking for 24 hours or days, respectively, at 37° C. in Sabouraud Dextrose Broth (SDB, DIFCO). To obtain midlogarithmic phase organisms, 1.0 ml of overnight culture was inoculated into 50 ml of SDB and incubated for 3 hours (*C. albicans*) or overnight (*C. neoformans*) with shaking. The cultures were centrifuged at 10,000 rpm for 10 minutes at 4° C., washed with cold 10 mM phosphate buffer, pH 7.4, and resuspended in cold buffer to a concentration of $1 \times 10^7$ cells/ml. The fungicidal assay mixture contained 30 1 of the phosphate buffer, 10 μl ($1 \times 10^5$ cells) of the fungal stock suspension, and 10 μl of peptide giving final peptide concentrations of 0 to 50 μg/ml. Incubations were carried out at 37° C. for 60 minutes, after which a 30 μl aliquot was removed and diluted 10, 100, and 1000-fold. Duplicate 100 μl samples of each dilution were spread onto SDB plates and incubated for 18 hours at 37° C. Plates were incubated for 1 or 2 days at 37° C. Surviving organisms were quantitated by colony counting using a Darkfield Colony Counter (Quebec).

Figure 15:
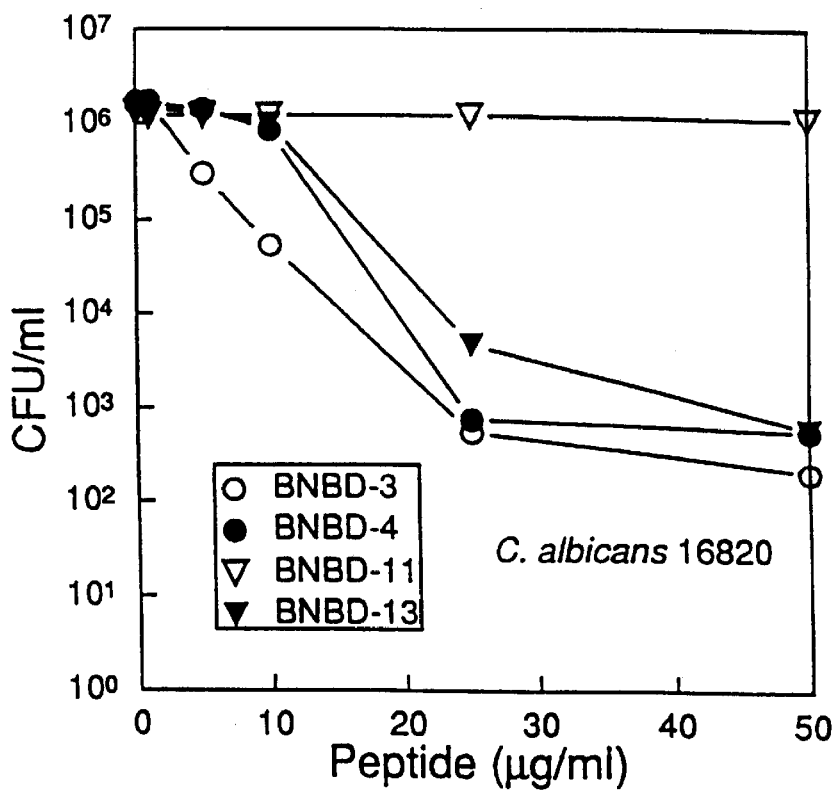
FIG. 15 shows the fungicidal activity of BNBD 3, 4, 11, and 13 against *Candida albicans*.

As shown in the accompanying figures, more than 99.9% of the *C. albicans* cells were killed in 60 minutes with 50 μg/ml of BNBD-3, -4 and -13 (FIG. 15). Interestingly, BNBD-11 was completely inactive at these concentrations.

Figure 16:
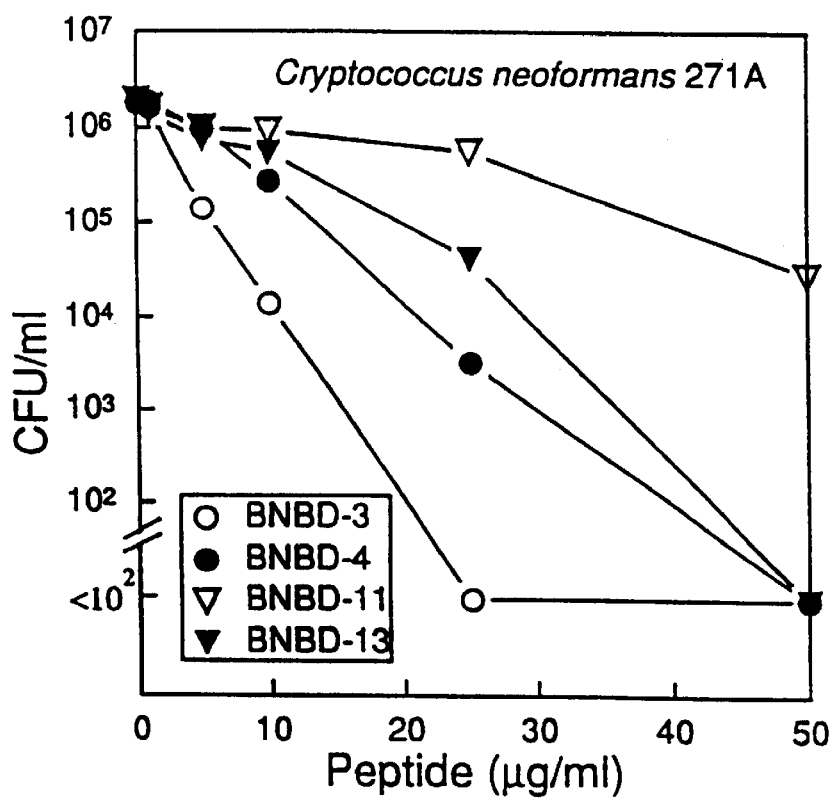
FIG. 16 shows the fungicidal activity of BNBD 3, 4, 11, and 13 against *Cryptococcus neoformans*.
Figure 17:
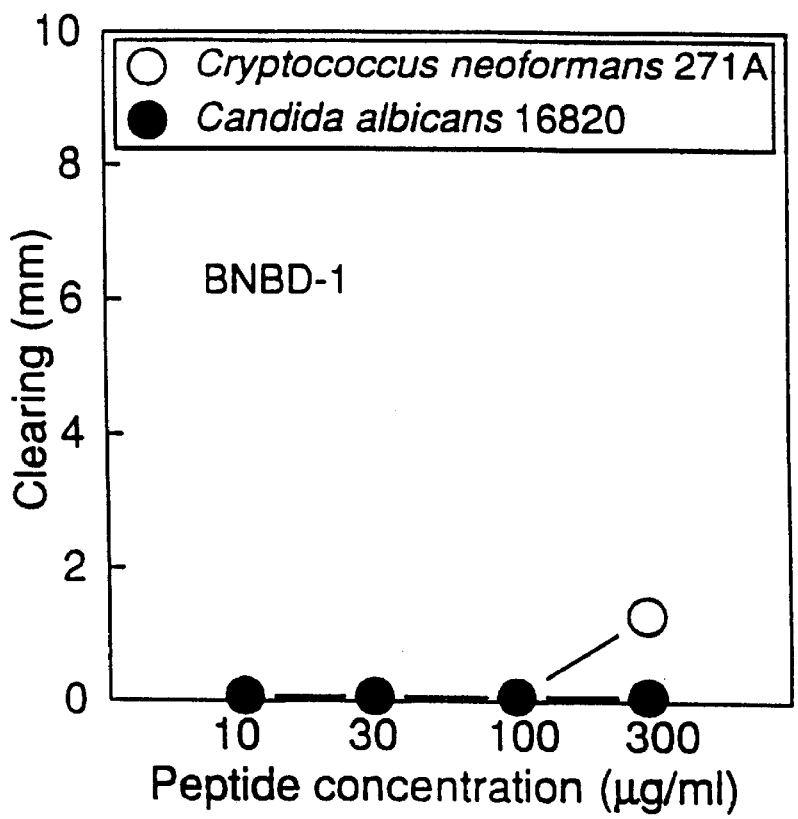
FIG. 17–31 show the antifungal activities of β-defensins.
Figure 18:
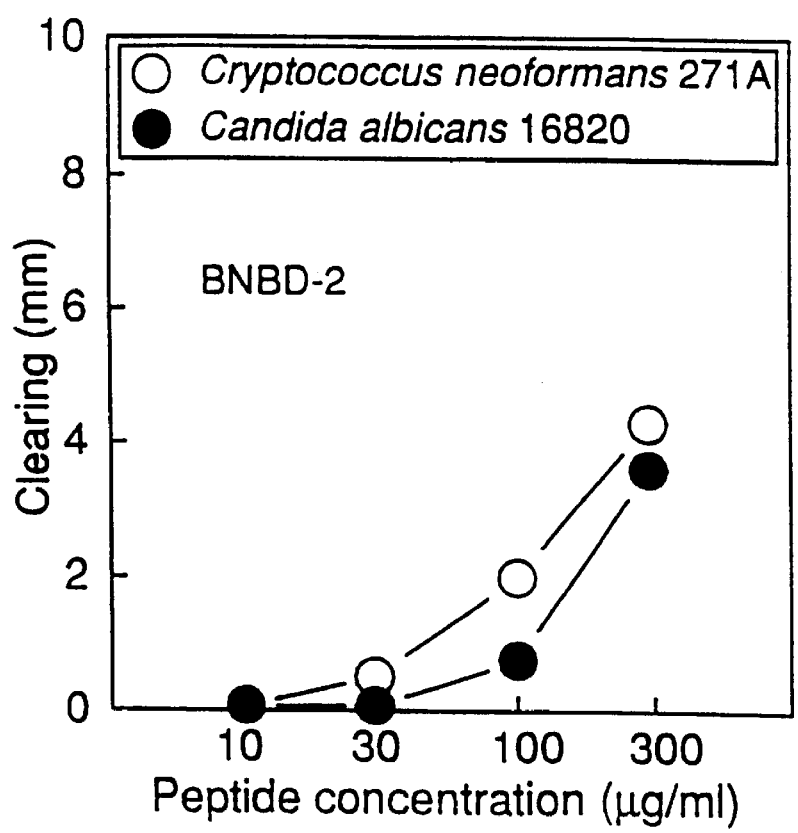
Figure 19:
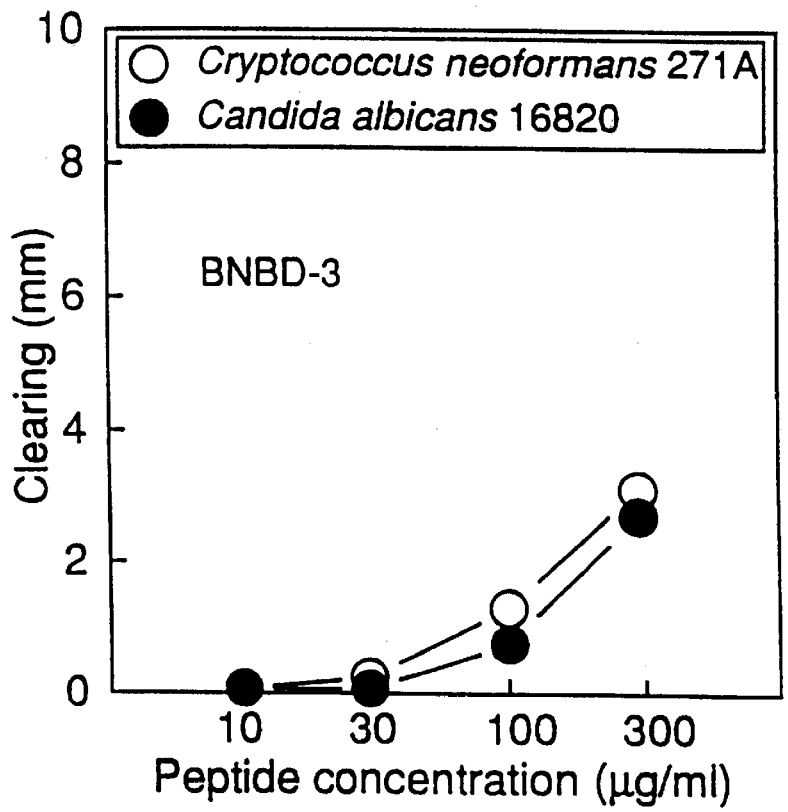
Figure 20:
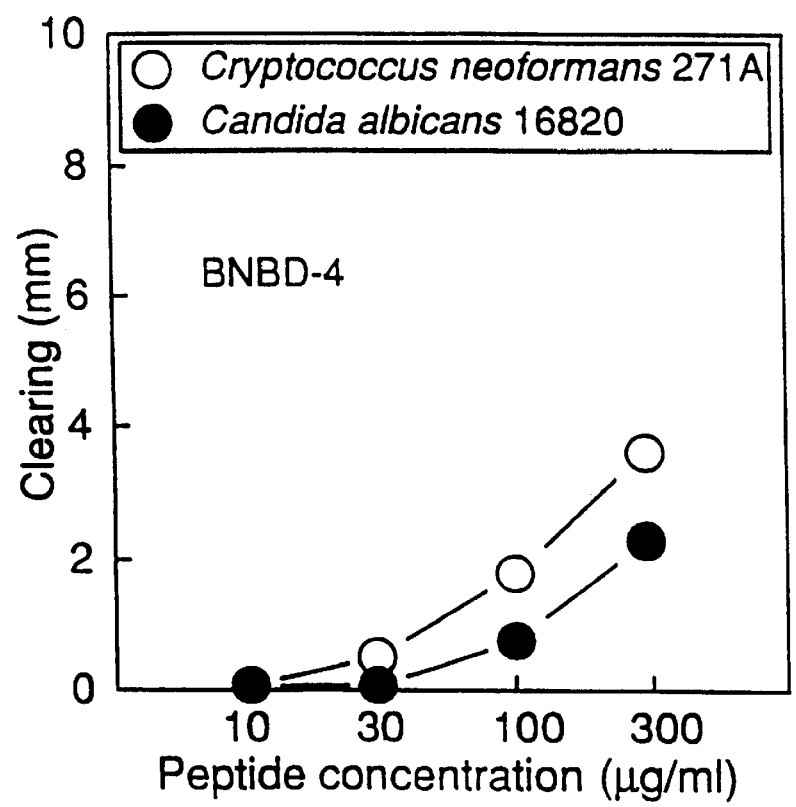
Figure 21:
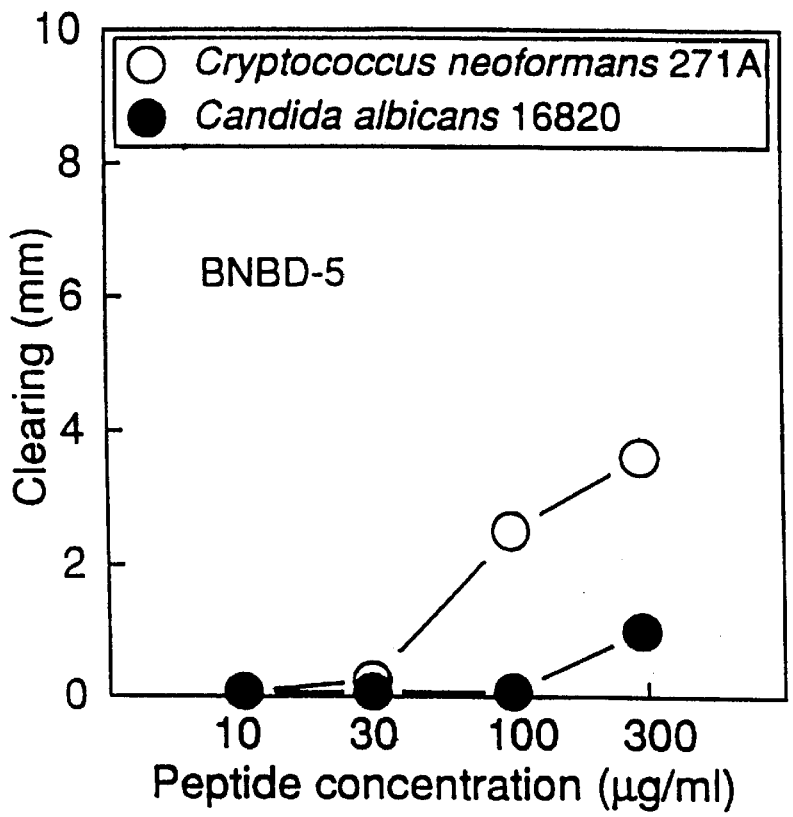
Figure 22:
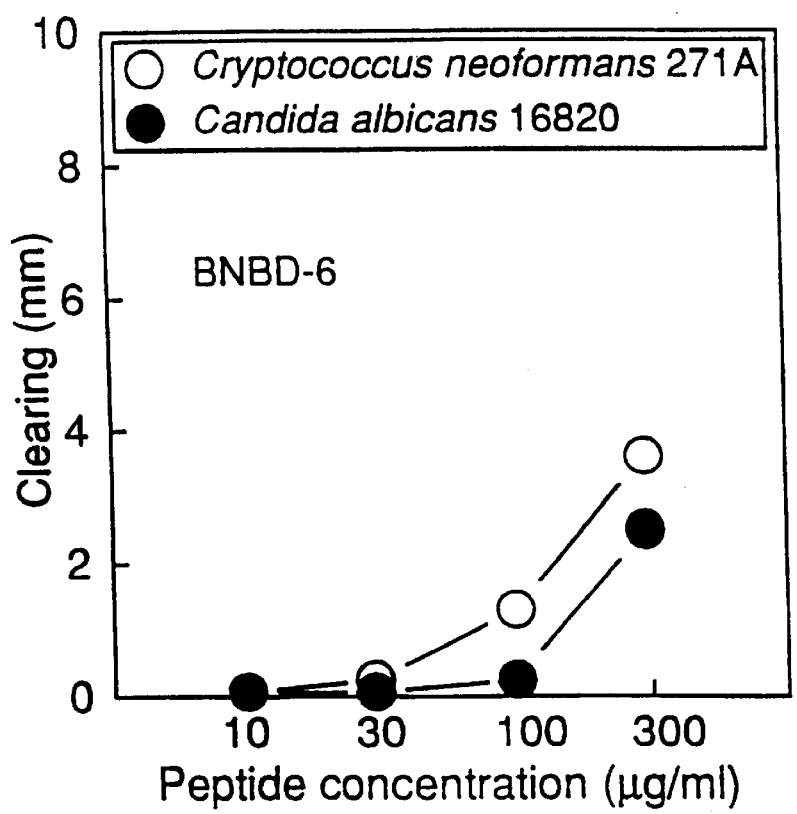
Figure 23:
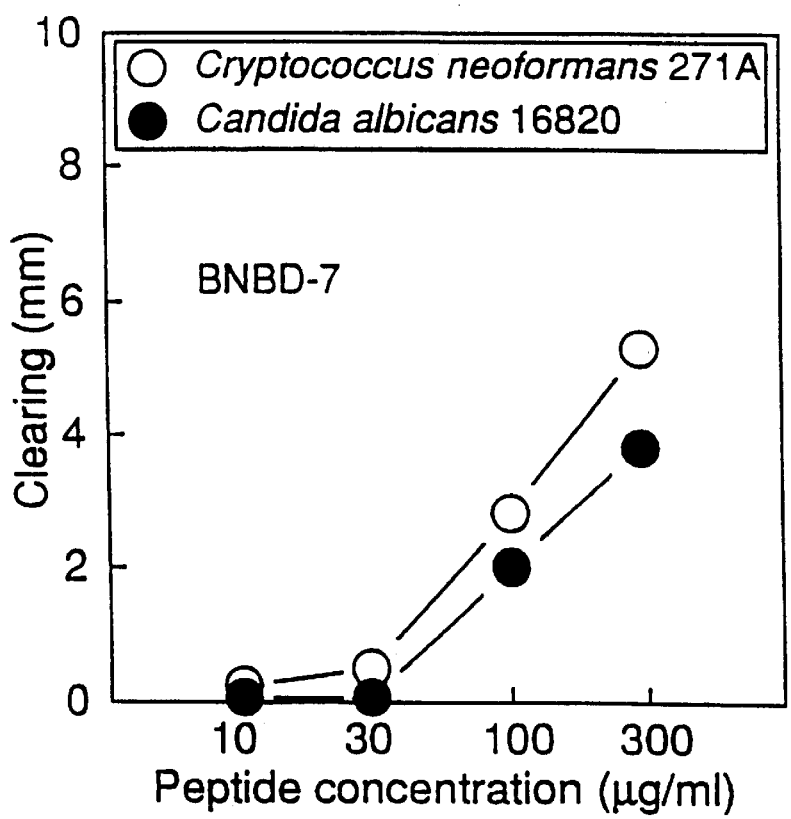
Figure 24:
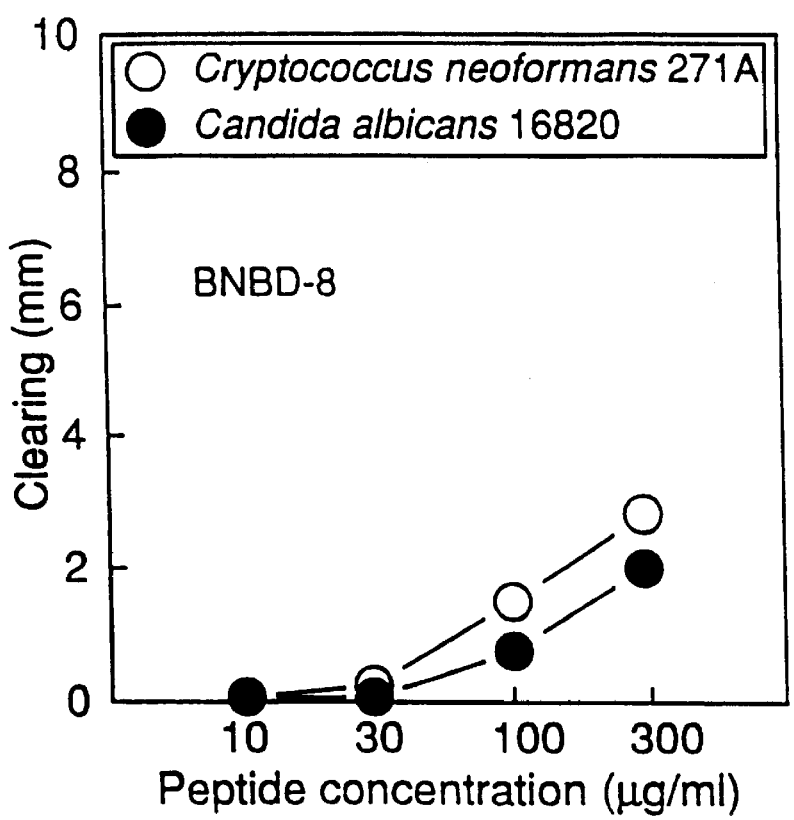
Figure 25:
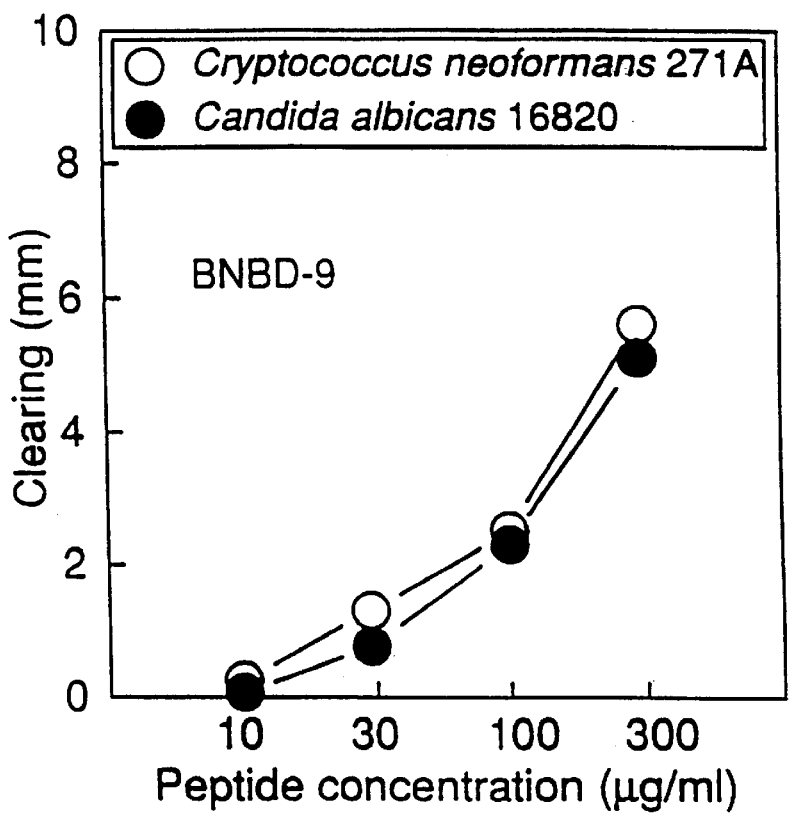
Figure 26:
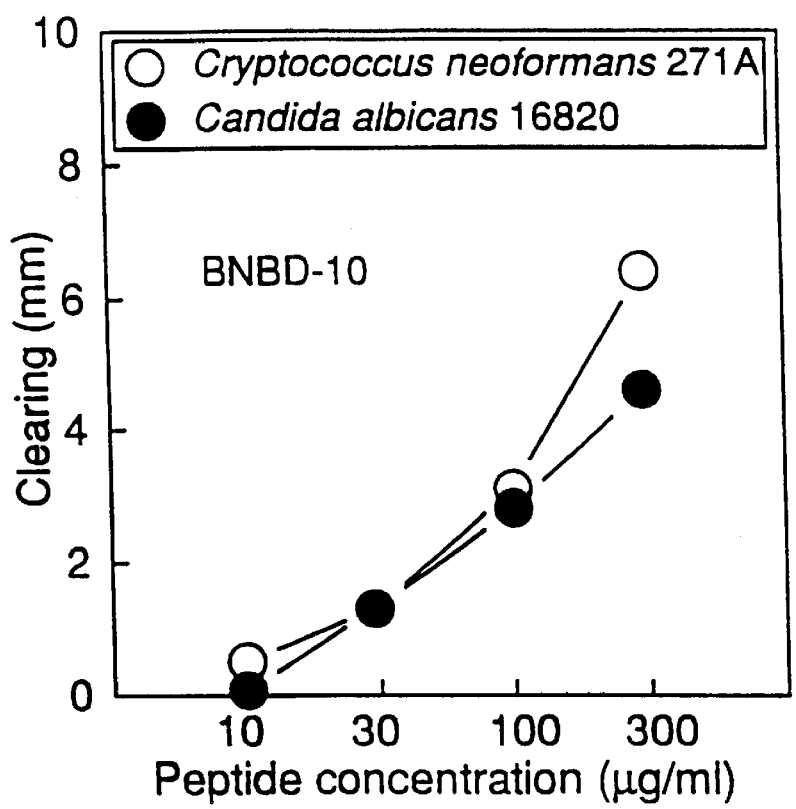
Figure 27:
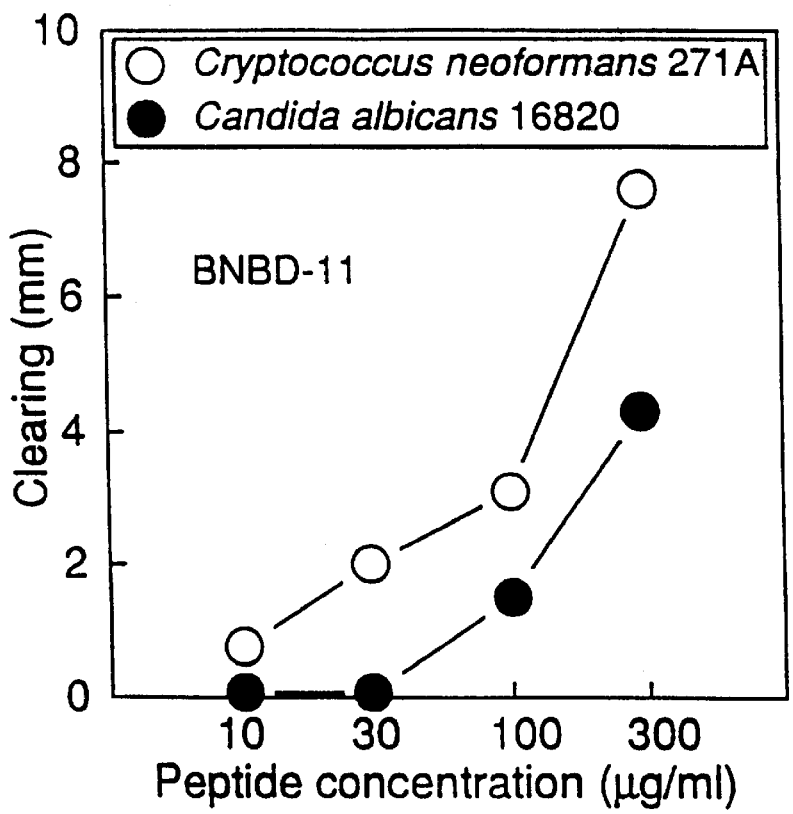
Figure 28:
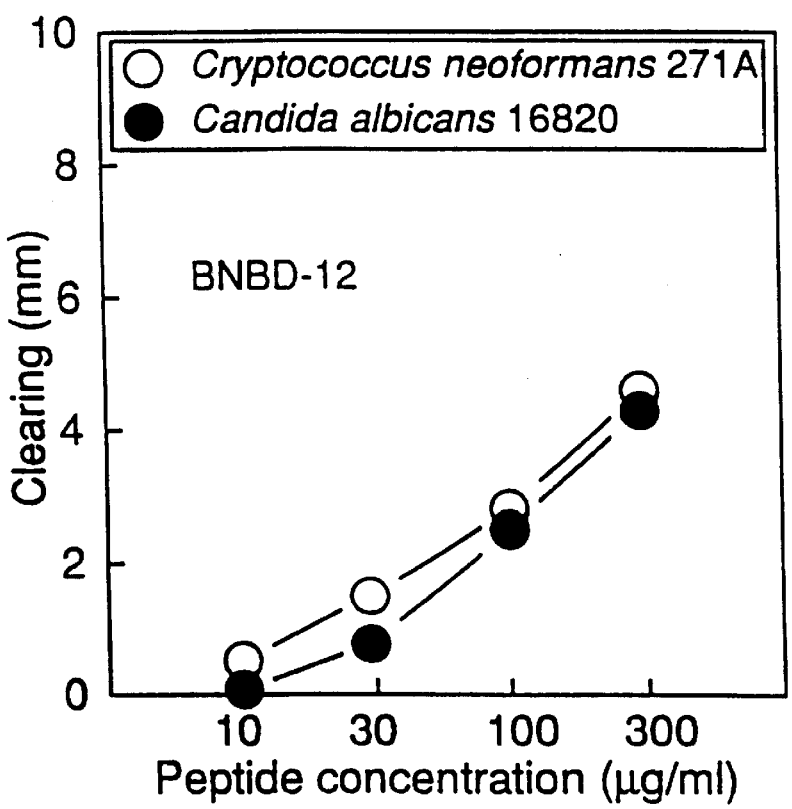
Figure 29:
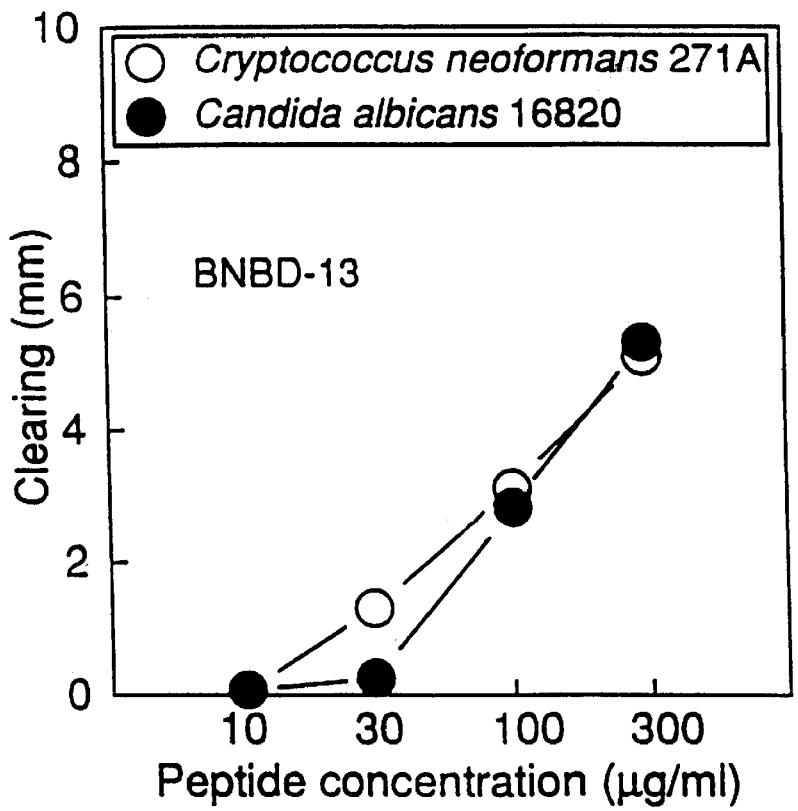
Figure 30:
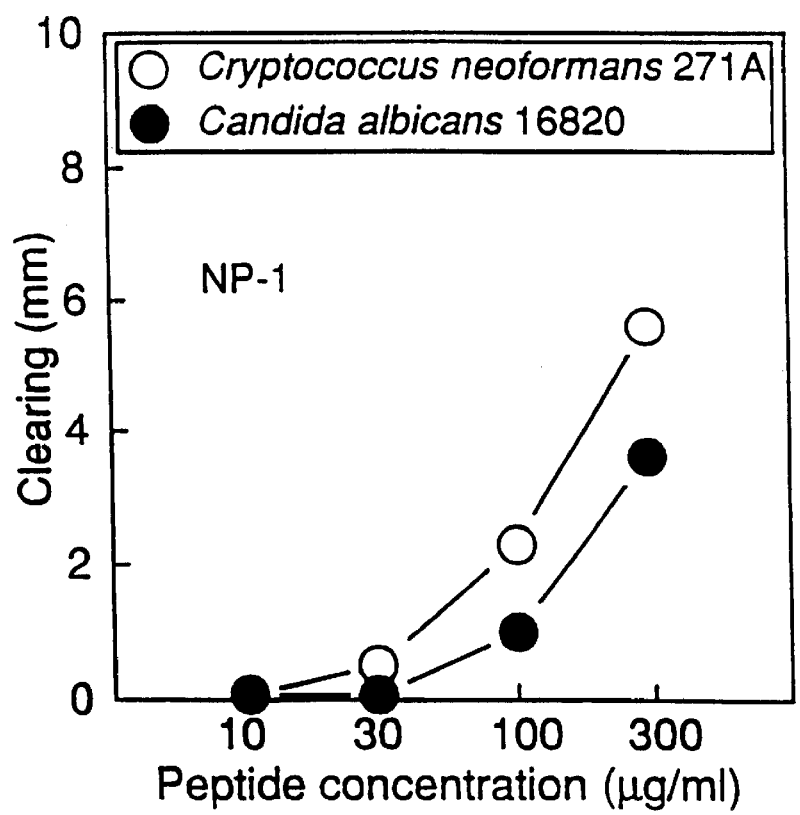
Figure 31:
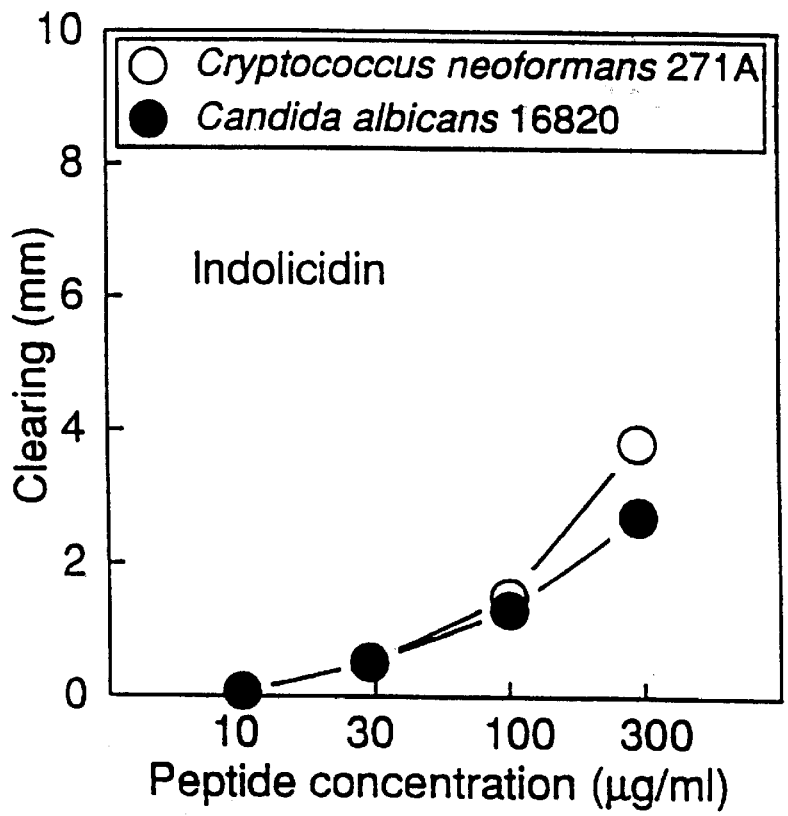
Figure 32:
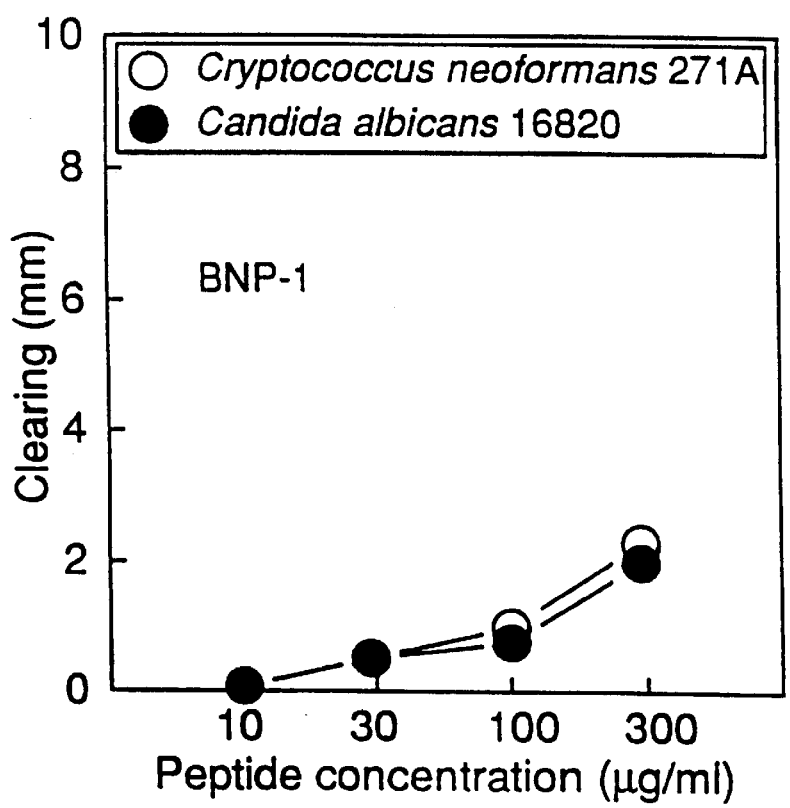

BNBD-3 was the most potent of the four beta-defensins defensins against *C. neoformans*, though BNBD-4 and -13 were equally effective at 50 μl/ml (FIG. 16). By comparison, BNBD-11 was substantially less active.

EXAMPLE VII

Antifungal Activities of Beta-Defensins

Ten ml of warm (42° C.) 1% agarose containing 0.03% (w/v) Sabouraud Dextrose Broth (SDB) was inoculated with 1×106 midlogarithmic phase C. *algicans* 16820 or C. *neoformans* 271A, and the seeded agarose was immediately poured into 9.5 cm square petri dishes. Sterile wells (4 mm) were formed in the solidified agarose, and 5 µl samples of each peptide (dissolved in 0.01% acetic acid) were introduced into wells with a micropipettor. The concentration of peptide varied from 0 to 300 µg/ml. The plates were allowed to incubate for 3 hours at 37° C., after which time they were overlayed with 10 ml of warm 1% agarose containing 6% SDB. After 24 to 48 hours, zones of clearing around each well were measured and plotted as a function of beta-defensin concentration. The relative activities of the beta-defensins against both fungi are summarized in the accompanying figures (FIGS. 17–32).

---

We claim:

1. A substantially purified β-defensin peptide having antimicrobial activity, wherein said peptide comprises the consensus figure set forth in Sequence ID no. 14, contains between 38 and 42 amino acids having a net charge of between +4 to +10, but lacks three consecutive basic amino acids at the carboxyl terminus.

2. A biologically active fragment of the peptide of claim 1, comprising the consensus sequence set forth in Sequence ID no. 14.

3. The recombinant peptide encoded by a nucleic acid encoding the peptide of claim 1.

4. The peptide of claim 1, wherein said peptide is obtained from bovine neutrophils.

5. An antimicrobial composition containing one or more of the β-defensin peptides of claim 1 and a carrier.

6. An antibody that specifically binds to a β-defensin.

7. The antibody of claim 6, wherein said antibody is of polyclonal origin.

8. The antibody of claim 6, wherein said antibody is of monoclonal origin.

9. A nucleic acid having a sequence encoding the β-defensin peptide of claim 1.

* * * * *

UNITED STATES PATENT AND TRADEMARK OFFICE
CERTIFICATE OF CORRECTION

PATENT NO. : 5,821,224
DATED : Oct. 13, 1998
INVENTOR(S) : Selsted et al.

It is certified that error appears in the above-identified patent and that said Letters Patent is hereby corrected as shown below:

In column 1, line 5, please delete "5,459,236" and replace therefor with --5,459,235--.

In column 2, line 14, after "beta-defensins" please insert a period.

In column 2, line 20, after "beta-defensins" please insert a period.

In column 2, line 30, please delete "outline" and replace therefor with --outlined--.

In column 3, line 47, please delete "a a" and replace therefor with --in a--.

In column 5, line 43, please delete "*Clonin:*" and replace therefor with --*Cloning:*--.

In column 7, line 21, please delete "ENBO" and replace therefor with --EMBO--.

In column 8, line 3, please delete "alos" and replace therefor with --also--.

In column 12, line 2, please delete "pg/ml," and replace therefor with --µg/ml,--.

UNITED STATES PATENT AND TRADEMARK OFFICE
CERTIFICATE OF CORRECTION

PATENT NO. : 5,821,224
DATED : Oct. 13, 1998
INVENTOR(S) : Selsted et al.

It is certified that error appears in the above-identified patent and that said Letters Patent is hereby corrected as shown below:

In column 13, line 34, please delete "by in" and replace therefor with --by * in--.

In column 14, line 10, please delete "DSD" and replace therefor with --SDS--.

In Table I, under the column BNBD-3, please delete "4009" in the $MW^f$ section, and replace therefor with --4809--.

In Table I, under the column BNBD-6, please delete "$(1)^e$" in the Trp section, and replace therefor with --$(1)^e$--.

In Table I, under the column BNBD-7, please delete "4.99(5) in the Gly section and replace therefor with --4.98(5)--.

In Table I, under the column BNBD-11, please delete (I) in the Glu section and replace therefor with --(1)--.

In Table I-continued, please delete "$^d$Values" and replace therefor with --$^a$Values--.

UNITED STATES PATENT AND TRADEMARK OFFICE
CERTIFICATE OF CORRECTION

PATENT NO. : 5,821,224
DATED : Oct. 13, 1998
INVENTOR(S) : Selsted et al.

It is certified that error appears in the above-identified patent and that said Letters Patent is hereby corrected as shown below:

In column 20, line 50, please delete "30 1" and replace therefor with --30 µl--.

In column 21, line 6, please delete "1X106" and replace therefor with --1X10$^6$--.

In column 21, line 6, please delete "*algicans*" and replace therefor with --*albicans*--.

Signed and Sealed this

Twenty-third Day of January, 2001

Attest:

*Attesting Officer*

Q. TODD DICKINSON
*Commissioner of Patents and Trademarks*

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Asp  Phe  Ala  Ser  Cys  His  Thr  Asn  Gly  Gly  Ile  Cys  Leu  Pro  Asn  Arg
  1              5                         10                          15
Cys  Pro  Gly  His  Met  Ile  Gln  Ile  Gly  Ile  Cys  Phe  Arg  Pro  Arg  Val
              20                         25                          30
Lys  Cys  Cys  Arg  Ser  Trp
              35
```

( 2 ) INFORMATION FOR SEQ ID NO:2:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Val  Arg  Asn  His  Val  Thr  Cys  Arg  Ile  Asn  Arg  Gly  Phe  Cys  Val  Pro
  1              5                         10                          15
Ile  Arg  Cys  Pro  Gly  Arg  Thr  Arg  Gln  Ile  Gly  Thr  Cys  Phe  Gly  Pro
              20                         25                          30
Arg  Ile  Lys  Cys  Cys  Arg  Ser  Trp
              35                         40
```

( 2 ) INFORMATION FOR SEQ ID NO:3:

( i ) SEQUENCE CHARACTERISTICS:
        ( A ) LENGTH: 42 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Glu  Gly  Val  Arg  Asn  His  Val  Thr  Cys  Arg  Ile  Asn  Arg  Gly  Phe  Cys
  1              5                         10                          15
Val  Pro  Ile  Arg  Cys  Pro  Gly  Arg  Thr  Arg  Gln  Ile  Gly  Thr  Cys  Phe
              20                         25                          30
```

```
          Gly  Pro  Arg  Ile  Lys  Cys  Cys  Arg  Ser  Trp
                    35                  40
```

(2) INFORMATION FOR SEQ ID NO:4:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO:4:

```
Glu  Arg  Val  Arg  Asn  Pro  Gln  Ser  Cys  Arg  Trp  Asn  Met  Gly  Val  Cys
 1                    5                       10                          15
Ile  Pro  Phe  Leu  Cys  Arg  Val  Gly  Met  Arg  Gln  Ile  Gly  Thr  Cys  Phe
                    20                       25                          30
Gly  Pro  Arg  Val  Pro  Cys  Cys  Arg  Arg
               35                  40
```

(2) INFORMATION FOR SEQ ID NO:5:

(i) SEQUENCE CHARACTERISTICS:
        (A) LENGTH: 40 amino acids
        (B) TYPE: amino acid
        (D) TOPOLOGY: linear (ii) MOLECULE TYPE: peptide (xi) SEQUENCE DESCRIPTION: SEQ ID NO:5:

```
Glu  Val  Val  Arg  Asn  Pro  Gln  Ser  Cys  Arg  Trp  Asn  Met  Gly  Val  Cys
 1                    5                       10                          15
Ile  Pro  Ile  Ser  Cys  Pro  Gly  Asn  Met  Arg  Gln  Ile  Gly  Thr  Cys  Phe
                    20                       25                          30
Gly  Pro  Arg  Val  Pro  Cys  Cys  Arg
               35                  40
```

(2) INFORMATION FOR SEQ ID NO:6:

(i) SEQUENCE CHARACTERISTICS:
        (A) LENGTH: 42 amino acids
        (B) TYPE: amino acid
        (D) TOPOLOGY: linear (ii) MOLECULE TYPE: peptide (xi) SEQUENCE DESCRIPTION: SEQ ID NO:6:

```
Glu  Gly  Val  Arg  Asn  His  Val  Thr  Cys  Arg  Ile  Tyr  Gly  Gly  Phe  Cys
 1                    5                       10                          15
Val  Pro  Ile  Arg  Cys  Pro  Gly  Arg  Thr  Arg  Gln  Ile  Gly  Thr  Cys  Phe
                    20                       25                          30
Gly  Arg  Pro  Val  Lys  Cys  Cys  Arg  Arg  Trp
               35                  40
```

(2) INFORMATION FOR SEQ ID NO:7:

(i) SEQUENCE CHARACTERISTICS:
        (A) LENGTH: 40 amino acids
        (B) TYPE: amino acid
        (D) TOPOLOGY: linear (ii) MOLECULE TYPE: peptide (xi) SEQUENCE DESCRIPTION: SEQ ID NO:7:

```
Glu  Gly  Val  Arg  Asn  Phe  Val  Thr  Cys  Arg  Ile  Asn  Arg  Gly  Phe  Cys
```

```
              1               5                    10                       15
              Val  Pro  Ile  Arg  Cys  Pro  Gly  His  Arg  Arg  Gln  Ile  Gly  Thr  Cys  Leu
                             20                         25                       30
              Gly  Pro  Arg  Ile  Lys  Cys  Cys  Arg
                             35                    40
```

(2) INFORMATION FOR SEQ ID NO:8:

(i) SEQUENCE CHARACTERISTICS:
        (A) LENGTH: 38 amino acids
        (B) TYPE: amino acid
        (D) TOPOLOGY: linear (ii) MOLECULE TYPE: peptide (xi) SEQUENCE DESCRIPTION: SEQ ID NO:8:

```
              Val  Arg  Asn  Phe  Val  Thr  Cys  Arg  Ile  Asn  Arg  Gly  Phe  Cys  Val  Pro
              1                   5                        10                       15
              Ile  Arg  Cys  Pro  Gly  His  Arg  Arg  Gln  Ile  Gly  Thr  Cys  Leu  Gly  Pro
                             20                         25                       30
              Gln  Ile  Lys  Cys  Cys  Arg
                             35
```

(2) INFORMATION FOR SEQ ID NO:9:

(i) SEQUENCE CHARACTERISTICS:
        (A) LENGTH: 40 amino acids
        (B) TYPE: amino acid
        (D) TOPOLOGY: linear (ii) MOLECULE TYPE: peptide (xi) SEQUENCE DESCRIPTION: SEQ ID NO:9:

```
              Glu  Gly  Val  Arg  Asn  Phe  Val  Thr  Cys  Arg  Ile  Asn  Arg  Gly  Phe  Cys
              1                   5                        10                       15
              Val  Pro  Ile  Arg  Cys  Pro  Gly  His  Arg  Arg  Gln  Ile  Gly  Thr  Cys  Leu
                             20                         25                       30
              Gly  Pro  Gln  Ile  Lys  Cys  Cys  Arg
                             35                    40
```

(2) INFORMATION FOR SEQ ID NO:10:

(i) SEQUENCE CHARACTERISTICS:
        (A) LENGTH: 40 amino acids
        (B) TYPE: amino acid
        (D) TOPOLOGY: linear (ii) MOLECULE TYPE: peptide (xi) SEQUENCE DESCRIPTION: SEQ ID NO:10:

```
              Glu  Gly  Val  Arg  Ser  Tyr  Leu  Ser  Cys  Trp  Gly  Asn  Arg  Gly  Ile  Cys
              1                   5                        10                       15
              Leu  Leu  Asn  Arg  Cys  Pro  Gly  Arg  Met  Arg  Gln  Ile  Gly  Thr  Cys  Leu
                             20                         25                       30
              Ala  Pro  Arg  Val  Lys  Cys  Cys  Arg
                             35                    40
```

(2) INFORMATION FOR SEQ ID NO:11:

(i) SEQUENCE CHARACTERISTICS:
        (A) LENGTH: 38 amino acids
        (B) TYPE: amino acid
        (D) TOPOLOGY: linear (ii) MOLECULE TYPE: peptide ( x i ) SEQUENCE DESCRIPTION: SEQ ID NO:11:

Gly Pro Leu Ser Cys Arg Arg Asn Gly Gly Val Cys Ile Pro Ile Arg
1               5                   10                  15

Cys Pro Gly Pro Met Arg Gln Ile Gly Thr Cys Phe Gly Arg Pro Val
            20                  25                  30

Lys Cys Cys Arg Ser Trp
            35

( 2 ) INFORMATION FOR SEQ ID NO:12:

( i ) SEQUENCE CHARACTERISTICS:
( A ) LENGTH: 38 amino acids
( B ) TYPE: amino acid
( D ) TOPOLOGY: linear ( i i ) MOLECULE TYPE: peptide ( x i ) SEQUENCE DESCRIPTION: SEQ ID NO:12:

Gly Pro Leu Ser Cys Gly Arg Asn Gly Gly Val Cys Ile Pro Ile Arg
1               5                   10                  15

Cys Pro Val Pro Met Arg Gln Ile Gly Thr Cys Phe Gly Arg Pro Val
            20                  25                  30

Lys Cys Cys Arg Ser Trp
            35

( 2 ) INFORMATION FOR SEQ ID NO:13:

( i ) SEQUENCE CHARACTERISTICS:
( A ) LENGTH: 42 amino acids
( B ) TYPE: amino acid
( D ) TOPOLOGY: linear ( i i ) MOLECULE TYPE: peptide ( x i ) SEQUENCE DESCRIPTION: SEQ ID NO:13:

Ser Gly Ile Ser Gly Pro Leu Ser Cys Gly Arg Asn Gly Gly Val Cys
1               5                   10                  15

Ile Pro Ile Arg Cys Pro Val Pro Met Arg Gln Ile Gly Thr Cys Phe
            20                  25                  30

Gly Arg Pro Val Lys Cys Cys Arg Ser Trp
            35                  40

( 2 ) INFORMATION FOR SEQ ID NO:14:

( i ) SEQUENCE CHARACTERISTICS:
( A ) LENGTH: 33 amino acids
( B ) TYPE: amino acid
( D ) TOPOLOGY: linear ( i i ) MOLECULE TYPE: peptide ( i x ) FEATURE:
( A ) NAME/KEY: Peptide
( B ) LOCATION: 1
( D ) OTHER INFORMATION: /note= "Y=Ser or Thr"

( i x ) FEATURE:
( A ) NAME/KEY: Peptide
( B ) LOCATION: one-of(3, 4, 6, 17, 18, 28)
( D ) OTHER INFORMATION: /note= "X = ANY AMINO ACID"

( i x ) FEATURE:
( A ) NAME/KEY: Peptide
( B ) LOCATION: one-of(8, 10, 25, 29)
( D ) OTHER INFORMATION: /note= "h = Leu, Ile, Val, or Phe"

( i x ) FEATURE:

(A) NAME/KEY: Peptide
(B) LOCATION: 27
(D) OTHER INFORMATION: /note= "Z = Pro or Arg"

(xi) SEQUENCE DESCRIPTION: SEQ ID NO:14:

Tyr Cys Xaa Xaa Asn Xaa Gly His Cys His Pro Ile Arg Cys Pro Gly
1               5                       10                      15

Xaa Xaa Arg Gln Ile Gly Thr Cys His Gly Glx Xaa His Lys Cys Cys
            20                      25                  30

Arg (2) INFORMATION FOR SEQ ID NO:15:

(i) SEQUENCE CHARACTERISTICS:
(A) LENGTH: 38 amino acids
(B) TYPE: amino acid
(D) TOPOLOGY: linear (ii) MOLECULE TYPE: peptide (xi) SEQUENCE DESCRIPTION: SEQ ID NO:15:

Asn Pro Val Ser Cys Val Arg Asn Lys Gly Ile Cys Val Pro Ile Arg
1               5                       10                      15

Cys Pro Gly Ser Met Lys Gln Ile Gly Thr Cys Val Gly Arg Ala Val
            20                      25                  30

Lys Cys Cys Arg Lys Lys
            35

(2) INFORMATION FOR SEQ ID NO:16:

(i) SEQUENCE CHARACTERISTICS:
(A) LENGTH: 38 amino acids
(B) TYPE: amino acid
(D) TOPOLOGY: linear (ii) MOLECULE TYPE: peptide (xi) SEQUENCE DESCRIPTION: SEQ ID NO:16:

Gly Pro Leu Ser Cys Gly Arg Asn Gly Gly Val Cys Ile Pro Ile Arg
1               5                       10                      15

Cys Pro Val Pro Met Arg Gln Ile Gly Thr Cys Phe Gly Arg Pro Val
            20                      25                  30

Lys Cys Cys Arg Ser Trp
            35

(2) INFORMATION FOR SEQ ID NO:17:

(i) SEQUENCE CHARACTERISTICS:
(A) LENGTH: 11 amino acids
(B) TYPE: amino acid
(D) TOPOLOGY: linear (ii) MOLECULE TYPE: peptide (xi) SEQUENCE DESCRIPTION: SEQ ID NO:17:

Gln Ile Gly Thr Cys Phe Gly Arg Pro Val Lys
1               5                       10

(2) INFORMATION FOR SEQ ID NO:18:

(i) SEQUENCE CHARACTERISTICS:
(A) LENGTH: 9 amino acids
(B) TYPE: amino acid
(D) TOPOLOGY: linear (ii) MOLECULE TYPE: peptide ( x i ) SEQUENCE DESCRIPTION: SEQ ID NO:18:

Asn Gly Gly Val Cys Ile Pro Ile Arg
1               5

( 2 ) INFORMATION FOR SEQ ID NO:19:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:19:

Pro Val Pro Met Arg
1               5

( 2 ) INFORMATION FOR SEQ ID NO:20:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:20:

Pro Thr His Gly
1

( 2 ) INFORMATION FOR SEQ ID NO:21:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: one-of(1, 2, 3, 6, 7, 9, 11, 13, 20, 21, 28,
                31, 32)
        ( D ) OTHER INFORMATION: /note= "X = Any Amino Acid"

( i x ) FEATURE:
        ( A ) NAME/KEY: Peptide
        ( B ) LOCATION: 4
        ( D ) OTHER INFORMATION: /note= "Y = Ser or Thr"

( i x ) FEATURE:
        ( A ) NAME/KEY: Peptide
        ( B ) LOCATION: 30
        ( D ) OTHER INFORMATION: /note= "Z = Pro or Arg"

( x i ) SEQUENCE DESCRIPTION: SEQ ID NO:21:

Xaa Xaa Xaa Tyr Cys Xaa Xaa Asn Xaa Gly Xaa Cys Xaa Pro Ile Arg
1               5                       10                      15

Cys Pro Gly Xaa Xaa Arg Gln Ile Gly Thr Cys Xaa Gly Glx Xaa Xaa
            20              25                      30

Lys Cys Cys Arg
            35

( 2 ) INFORMATION FOR SEQ ID NO:22:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( i x ) FEATURE:
    ( A ) NAME/KEY: Peptide
    ( B ) LOCATION: one-of(1, 2, 4, 6, 7, 8, 9, 11, 12, 13, 14, 16,
        17, 19, 21, 22, 23, 24, 25, 26, 27, 28, 29)
    ( D ) OTHER INFORMATION: /note= "X = ANY AMINO ACID"

( x i ) SEQUENCE DESCRIPTION: SEQ ID NO:22:

| Xaa | Xaa | Cys | Xaa | Cys | Xaa | Xaa | Xaa | Xaa | Cys | Xaa | Xaa | Xaa | Xaa | Arg | Xaa |
|---|---|---|---|---|---|---|---|---|---|---|---|---|---|---|---|
| 1 | | | | 5 | | | | | 10 | | | | | 15 | |
| Xaa | Gly | Xaa | Cys | Xaa | Xaa | Xaa | Xaa | Xaa | Xaa | Xaa | Xaa | Xaa | Cys | Cys | |
| | | | 20 | | | | | 25 | | | | | 30 | | |